(12) United States Patent
García Collazo et al.

(10) Patent No.: US 11,731,963 B2
(45) Date of Patent: *Aug. 22, 2023

(54) PROCESS FOR PREPARING 5-[[4-[2-[5-(1-HYDROXYETHYL)-2-PYRIDINYL]ETHOXY]PHENYL]-METHYL]-2,4-THIAZOLIDINEDIONE AND SALTS THEREOF

(71) Applicant: Minoryx Therapeutics S.L., Barcelona (ES)

(72) Inventors: Ana Maria García Collazo, Barcelona (ES); Wolter Ten Hoeve, Groningen (NL); Johannes Nicolaas Koek, Groningen (NL); Johannes B. M. Rewinkel, Oss (NL); Sander De Wilde, Oss (NL)

(73) Assignee: Minoryx Therapeutics S.L., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,838

(22) Filed: Sep. 20, 2021

(65) Prior Publication Data
US 2022/0204496 A1 Jun. 30, 2022

Related U.S. Application Data

(63) Continuation of application No. 16/470,866, filed as application No. PCT/IB2017/058374 on Dec. 22, 2017, now Pat. No. 11,124,505.

(30) Foreign Application Priority Data

Dec. 23, 2016 (EP) .................................. 16382648

(51) Int. Cl.
   C07D 417/12 (2006.01)
   C07D 213/127 (2006.01)
   C07F 7/10 (2006.01)

(52) U.S. Cl.
   CPC ....... C07D 417/12 (2013.01); C07D 213/127 (2013.01); C07F 7/10 (2013.01)

(58) Field of Classification Search
   CPC .................................................. C07D 417/12
   See application file for complete search history.

(56) References Cited

U.S. PATENT DOCUMENTS

| | | | |
|---|---|---|---|
| 5,952,495 | A | 9/1999 | Huang et al. |
| 6,100,403 | A | 8/2000 | Saito et al. |
| 11,124,505 | B2 | 9/2021 | Garcia Collazo et al. |
| 2008/0312411 | A1 | 12/2008 | Wolf et al. |
| 2009/0247560 | A1 | 10/2009 | Ando et al. |

FOREIGN PATENT DOCUMENTS

| | | |
|---|---|---|
| EP | 2149550 A1 | 2/2010 |
| WO | WO-9218501 A1 | 10/1992 |
| WO | WO-9802033 A1 | 1/1998 |
| WO | WO-2005058827 A1 | 6/2005 |
| WO | WO-2006035195 A1 | 4/2006 |
| WO | WO-2013163241 A1 | 10/2013 |
| WO | WO-2014152843 A1 | 9/2014 |
| WO | WO-2015150476 A1 | 10/2015 |

OTHER PUBLICATIONS

Mukund P Sibi and Gregory R. Cook Chapter 12 "Copper Lewis Acids in Organic Synthesis" in Lewis Acids in Organic Synthesis Edited by Hisashi Yamamoto 0 Wiley-VCH Verlag GmbH 2000.*
Green, T.W., and Wuts, P.G.M., "Protective Groups in Organic Synthesis," p. 114, John Wiley & Sons, 1999.
International Preliminary Report on Patentability for Application No. PCT/IB2017/058374, The International Bureau of WIPO, Switzerland, dated Jun. 2019, 6 pages.
International Search Report and Written Opinion for International Application No. PCT/IB2017/058374, European Patent Office, Netherlands, dated Apr. 26, 2018.
Maeshiba, Y., et al., "Disposition of the New Antidiabetic Agent Pioglitazone in Rats, Dogs, and Monkeys," Arzneimittel-Forschung 47(1):29-35, Editio Cantor, Gemany (1997).
Sohda, T., et al., "Studies on Antidiabetic Agents. XII. Synthesis and Activity of the Metabolites of (+/−)-5(−)[p(−)[2-(5-ethyl-2-pyridyl)ethoxy]benzyl]-2,4-thiazolidinedione (Pioglitazone)," Chemical and Pharmaceutical Bulletin 43(12):2168-2172, Pharmaceutical Society of Japan, Japan (1995).
Tanis, S.P., et al., "Synthesis and Biological Activity of Metabolites of the Antidiabetic, Antihyperglycemic Agent Pioglitazone," Journal of Medicinal Chemistry 39(26):5053-5063, American Chemical Society, United States (Dec. 1996).

(Continued)

*Primary Examiner* — David K O'Dell
(74) *Attorney, Agent, or Firm* — Sterne, Kessler, Goldstein & Fox P.L.L.C.

(57) ABSTRACT

The disclosure provides a process of making the compound of Formula I, and pharmaceutically acceptable salts thereof; and the process of making the intermediate of Formula III; wherein PG is as defined as set forth in the specification.

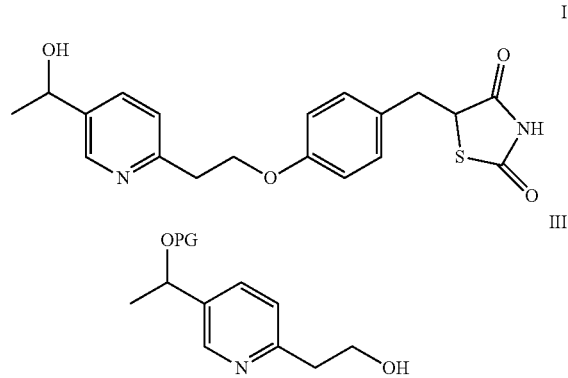

18 Claims, No Drawings

(56) References Cited

OTHER PUBLICATIONS

Wuts, P.G.M. and Greene, T.W., "Protection for Phenols and Catechols," in Greene's Protective Groups in Organic Synthesis, 4th Ed., Wuts, P.G.M. and Greene, T.W., eds., pp. 367-430, John Wiley & Sons, Inc., United States (2007).

Wuts, P.G.M. and Greene, T.W., "Protection for the Hydroxyl Group, Including 1,2- and 1,3-Diols," in Greene's Protective Groups in Organic Synthesis, 4th Ed., Wuts, P.G.M. and Greene, T.W., eds., pp. 16-366, John Wiley & Sons, Inc., United States (2007).

Wang, X., et al., Selective monolithiation of 2, 5-dibromopyridine with butyllithium., Tetrahedron Letters 41(22): 4335-4338, Elsevier, Netherlands (2000).

Ila, H., et al., Preparation and reactions of heteroaryl organomagnesium compounds., Chemistry Letters 35(1): 2-7, The Chemical Society of Japan, Japan (2006).

Trecourt, F., et al., "Catalyzed Metalation Applied to 2-Methoxypyridine" J. Org. Chem. 53(7):1367-1371, American Chemical Society, United States (1988).

Joule, J.A. and Mills, K., "Organometallic Heterocyclic Chemistry" in Heterocyclic Chemistry, pp. 39, 5th Ed., John Wiley & Sons Ltd., United Kingdom (2010).

Gros, P., et al., "nBuLi/Lithium Aminoalkoxide Aggregates: New and Promising Lithiating Agents for Pyridine Derivatives," Eur. J. Org. Chem. 2002:3375-3383, Wiley-VCH, Germany (2002).

Manolikakes, S.M., et al., "Regioselective Functionalization of Pyridines using a Directed Metalation or a Halogen/Metal Exchange," Z. Naturforsch 68b:411-422, Walter de Gruyter, Berlin (2013).

Marsais, F., et al., "Synthesis and structural study of 2,5-dihydropyridines. Competitive metalation of 2-fluoropyridine," J. Org. Chem. 46(22):4494-4497, American Chemical Society, United States (1981).

Bobbio, C., et al., "Removal of Fluorine from and Introduction of Fluorine into Polyhalopyridines: an Exercise in Nucleophilic Hetarenic Substitution," Chem. Eur. J. 11:1903-1910, Wiley-VCH, Germany (2005).

\* cited by examiner

PROCESS FOR PREPARING 5-[[4-[2-[5-(1-HYDROXYETHYL)-2-PYRIDINYL]ETHOXY]PHENYL]-METHYL]-2,4-THIAZOLIDINEDIONE AND SALTS THEREOF

CROSS-REFERENCE TO RELATED APPLICATION

This application claims priority to European Application No. EP16382648.0, filed on Dec. 23, 2016, the entirety of which is incorporated by reference herein.

FIELD OF DISCLOSURE

The present application relates to a novel process for preparing 5-[[4-[2-[5-(1-hydroxyethyl)-2-pyridinyl]ethoxy]phenyl]methyl]-2,4-thiazolidinedione, also known as the M-IV metabolite of pioglitazone, and pharmaceutically acceptable salts thereof.

BACKGROUND OF THE RELATED ART

Pioglitazone is a drug marketed for use in the treatment of diabetes mellitus type 2. Pioglitazone is a potent agonist for peroxisome proliferator-activated receptor-gamma (PPARγ) and it has been proposed for the treatment of some neurodegenerative diseases including Alzheimer's, Parkinson's disease, ALS and Friedreich's ataxia. Pioglitazone has been associated with unwanted side effects including cardiovascular effects, fluid retention, weight gain and bladder cancer. High doses of pioglitazone are therefore undesirable as high systemic exposure would be likely to result in serious side effects.

Pioglitazone is a "dirty" drug which is converted to many metabolites in vivo. The metabolic pathway of pioglitazone after oral administration has been studied in several animal species and in humans and the metabolites have been described in the literature (see e.g. Sohda et at, Chem. Pharm. Bull., 1995, 43(12), 2168-2172) and Maeshiba et al, Arzneim.-Forsch/Drug Res, 1997, 47 (I), 29-35). At least six metabolites have been identified, named M-I to M-VI. Amongst these metabolites, M-II, M-III and M-IV show some pharmacological activity but are less active than Pioglitazone in diabetic preclinical models.

5-[[4-[2-[5-(1-hydroxyethyl)-2-pyridinyl]ethoxy]phenyl]methyl]-2,4-thiazolidinedione has the following structure:

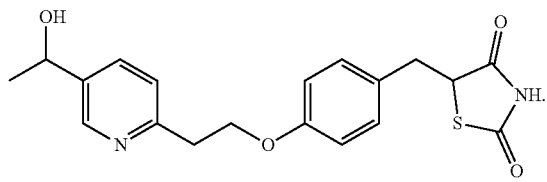 [SMILES: CC(O)c1ccc(CCOc2ccc(CC3SC(=O)NC3=O)cc2)nc1]

Tanis et al. (*J. Med. Chem.* 39(26):5053-5063 (1996)) describe the synthesis of 5-[[4-[2-[5-(1-hydroxyethyl)-2-pyridinyl]ethoxy]phenyl]methyl]-2,4-thiazolidinedione as follows:

Scheme 1

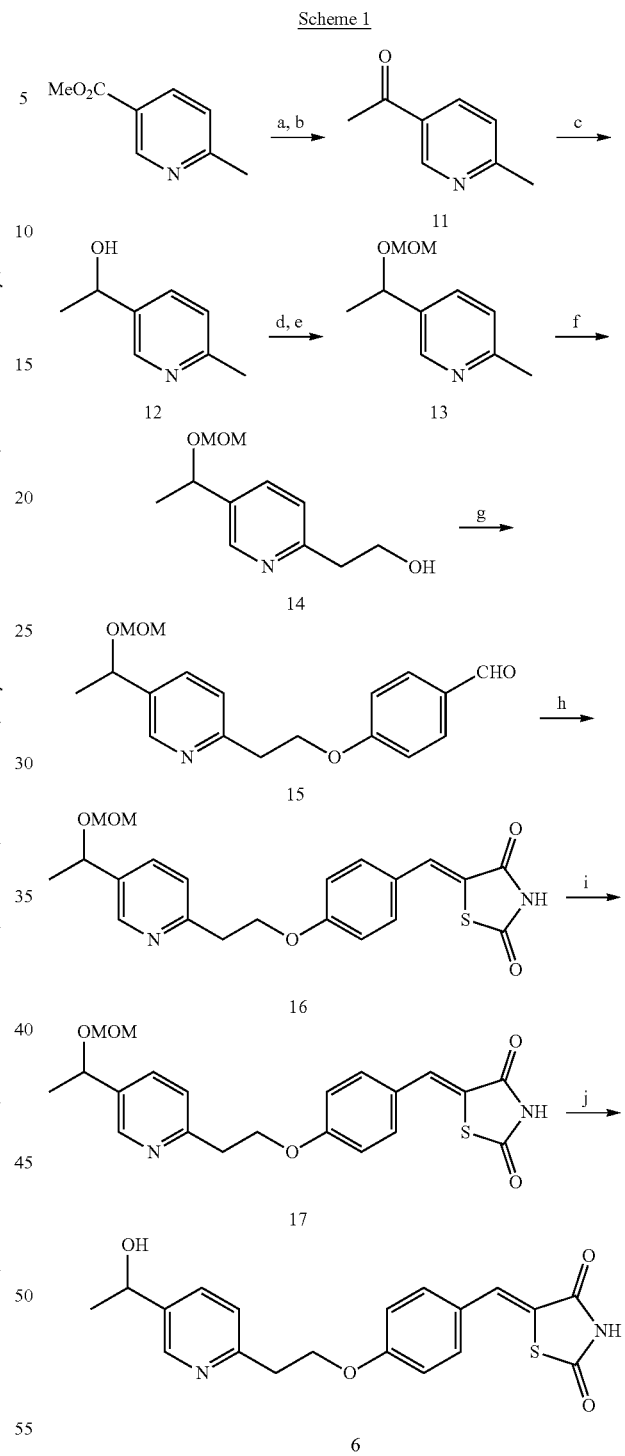

Tanis et al. describe that the intermediate 14 was obtained in a 27% yield by reacting compound 13 in an aqueous 37% formaldehyde at 170° C. for 6 hours. In this process, 5-[[4-[2-[5-(1-hydroxyethyl)-2-pyridinyl]ethoxy]phenyl]methyl]-2,4-thiazolidinedione (compound 6 in Scheme 1) was obtained in a 2.47% overall yield.

WO 2015/150476 A1 describes the use of 5-[[4-[2-[5-(1-hydroxyethyl)-2-pyridinyl]ethoxy]phenyl]methyl]-2,4-thiazolidinedione, and its pharmaceutically acceptable salts, in the treatment of central nervous system (CNS) disorders.

WO 2015/150476 A1 describes that 5-[[4-[2-[5-(1-hydroxy-ethyl)-2-pyridinyl]ethoxy]phenyl]methyl]-2,4-thiazolidin-edione was prepared according to the process of Tanis et al. (supra) where the intermediate corresponding to compound 14 of Tanis et al. was prepared similarly at 160° C. for 5 hours providing a 17% yield. The overall yield of 5-[[4-[2-[5-(1-hydroxyethyl)-2-pyridinyl]ethoxy]phenyl]methyl]-2,4-thiazolidinedione was about 1.5%.

Due to the low yield of the intermediate 2-[5-(I-methoxymethoxy-ethyl)pyridine-2-yl]ethanol, the process step for preparing this intermediate is critical for the overall yield of the product, 5-[[4-[2-[5-(1-hydroxyethyl)-2-pyridinyl]ethoxy]phenyl]methyl]-2,4-thiazolidinedione. In addition, the prior art process to obtain compound 14 is difficult to scale because the reaction is carried out in a pressure vessel at a very high temperature and it is a very dirty reaction.

Accordingly, the processes described in the art afford the product 5-[[4-[2-[5-(1-hydroxyethyl)-2-pyridinyl]ethoxy]phenyl]methyl]-2,4-thiazolidinedione only in a very low overall yield and, therefore, they are not suitable for large scale synthesis. In addition, the prior art process employs CH$_3$OCH$_2$Cl, a known carcinogen, for protecting the hydroxyl group in the key intermediate. There is a need for an improved process for synthesizing 5-[[4-[2-[5-(1-hydroxyethyl)-2-pyridinyl]ethoxy]phenyl]methyl]-2,4-thiazolidinedione, and its pharmaceutically acceptable salts.

BRIEF SUMMARY OF THE INVENTION

The present disclosure provides an improved process for preparing a compound of Formula I:

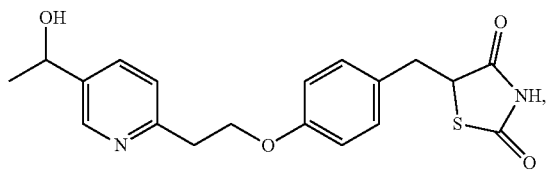

I

5-[[4-[2-[5-(1-hydroxyethyl)-2-pyridinyl]ethoxy]phenyl]methyl]-2,4-thiazolidinedione, and pharmaceutically acceptable salts thereof, collectively referred to herein as "Compounds of the Disclosure" (each is individually referred to hereinafter as a "Compound of the Disclosure").

An aspect of the present disclosure is directed to a process for preparing a synthetic intermediate having Formula III:

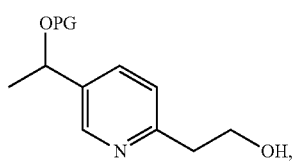

III wherein PG is a protecting group. In one embodiment, PG is a silyl protecting group, tetrahydropyranyl, methoxymethyl, or benzyl. In another embodiment, PG is a silyl protecting group, tetrahydropyranyl, or methoxymethyl. A compound having Formula III is used in processes of preparing Compounds of the Disclosure.

The process of preparing a compound having Formula III comprises reacting a compound of Formula II:

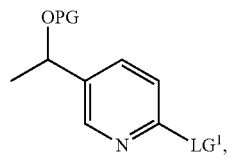

II wherein PG is a protecting group and LG$^1$ is a leaving group,
with ethylene oxide in the presence of
(a) an alkyl lithium and a copper(I)salt, or
(b) an alkyl lithium and a Lewis acid, and
a solvent,
to give a compound of Formula III:

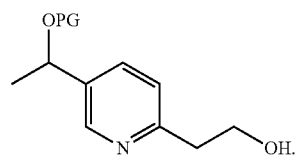

III

In one embodiment, the copper(I)salt is selected from the group consisting of copper(I)bromide, copper(I)chloride, and copper(I)iodide. In another embodiment, the copper(I)salt is copper(I)iodide.

In another embodiment, the Lewis acid is selected from the group consisting of AlBr$_3$, AlCl$_3$, FeBr$_3$, FeCl$_3$, SnCl$_4$, Ti(OiPr)$_4$, BF$_3$, BF$_3$.O(Et)$_2$, BBr$_3$, BCl$_3$, TiCl$_4$, and ZnCl$_2$. In another embodiment, the Lewis acid is selected from the group consisting of BF$_3$.O(Et)$_2$, BBr$_3$, BCl$_3$, TiCl$_4$, and ZnCl$_2$. In another embodiment, the Lewis acid is selected from the group consisting of BF$_3$.O(Et)$_2$, BBr$_3$ and BCl$_3$.

In another embodiment, the protect group is selected from the group consisting of a silyl protecting group, tetrahydropyranyl, methoxymethyl, and benzyl. In another embodiment, the protecting group is selected from the group consisting of a silyl protecting group, tetrahydropyranyl, and methoxymethyl. In another embodiment, the protecting group is a silyl protected group.

In another embodiment, the leaving group is —Br.

In another embodiment, the process of preparing a compound having Formula III comprises reacting a compound of Formula II:

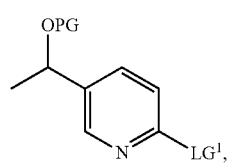

II wherein PG is a protecting group and LG$^1$ is a leaving group,
with ethylene oxide in the presence of
(a) an alkyl lithium and a copper(I)salt, e.g., copper(I)iodide, or (b) an alkyl lithium and a Lewis acid, e.g., BF$_3$.O(Et)$_2$, BBr$_3$ or BCl$_3$, and
a solvent,
to give a compound of Formula III:

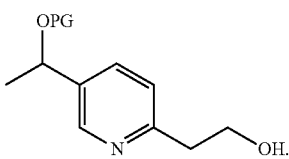

III

In one embodiment, the process of preparing a compound having Formula III comprises reacting a compound of Formula II:

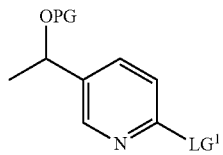

II wherein PG is a protecting group selected from the group consisting of a silyl protecting group, tetrahydropyranyl, methoxymethyl, and benzyl; and
LG$^1$ is a leaving group,
with ethylene oxide in the presence of
(a) an alkyl lithium and a copper(I)salt, e.g., copper(I) iodide; or
(b) an alkyl lithium and a Lewis acid selected from the group consisting of BF$_3$.O(Et)$_2$, BBr$_3$ and BCl$_3$, and
a solvent,
to give a compound of Formula III:

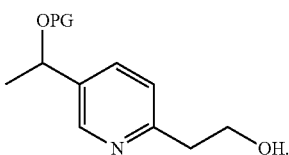

III

In one embodiment, the ethylene oxide, alkyl lithium, and copper(I)salt (e.g., copper(I)iodide) or the Lewis acid (collectively referred to as the "reagents") are added into the reaction mixture comprising the compound of Formula II at low temperature, e.g., at a temperature of about −20° C., about −25° C., about −30° C., about −35° C., about −40° C., about −45° C., about −50° C., about −55° C., about −60° C., about −65° C., about −70° C., or about −75° C. In another embodiment, the reagents are added while maintaining the temperature of the reaction mixture below −20° C. In another embodiment, the reagents are added while maintaining the temperature of the reaction mixture at about <−55° C.

In another embodiment, the ethylene oxide is added into the reaction mixture after first adding the alkyl lithium. In another embodiment, the ethylene oxide is added into the reaction mixture after adding the alkyl lithium and the copper(I)salt, e.g., copper(I)iodide, or the Lewis acid. In another embodiment, the reaction is conducted in the presence of alkyl lithium and copper(I)iodide. In another embodiment, the alkyl lithium and copper(I)iodide are added while maintaining the reaction temperature at about below −55° C. In another embodiment, the reaction is conducted in the presence of an alkyl lithium and a Lewis acid. In another embodiment, the Lewis acid is selected from the group consisting of BF$_3$.O(Et)$_2$, BBr$_3$ and BCl$_3$.

In another embodiment, the reaction mixture is allowed to warm to room temperature, e.g., about 20-25° C., after the addition of the reagents. In another embodiment, the reaction mixture is kept at 20° C.-25° C. for at least 4 hours. In another embodiment, the reaction mixture is kept at 20° C.-25° C. for at least 6 hours. In another embodiment, the reaction mixture is kept at 20° C.-25° C. for at least 8 hours. In another embodiment, the reaction mixture is kept at 20° C.-25° C. for at least 10 hours.

In another embodiment, the process of preparing a compound having Formula III comprises reacting a compound of Formula II:

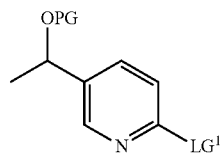

II wherein PG is a protecting group selected from the group consisting of a silyl protecting group, tetrahydropyranyl, and methoxymethyl; and
LG$^1$ is a leaving group,
with ethylene oxide in the presence of an alkyl lithium and copper(I)iodide, and
a solvent, wherein
the reaction temperature is maintained below −20° C. when adding the alkyl lithium and the copper(I)iodide into the reaction mixture,
to give a compound of Formula III:

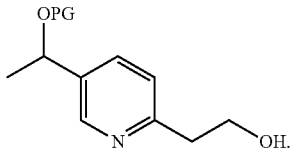

III

In one embodiment of this aspect of the disclosure, the ethylene oxide is added into the reaction mixture after first adding the alkyl lithium. In another embodiment of this aspect of the disclosure, the alkyl lithium and copper(I)salt, e.g., copper(I)iodide, are added while maintaining the reaction temperature at about <−55° C. In another embodiment, the reaction mixture is allowed to warm to room temperature, e.g., about 20-25° C., after the addition of the reagents. In another embodiment, the reaction mixture is kept at 20° C.-25° C. for at least 4 hours. In another embodiment, the reaction mixture is kept at 20° C.-25° C. for at least 6 hours. In another embodiment, the reaction mixture is kept at 20° C.-25° C. for at least 8 hours. In another embodiment, the reaction mixture is kept at 20° C.-25° C. for at least 10 hours.

In one embodiment, the solvent is selected from the group consisting of a non-polar organic solvent and polar organic solvent, or a mixture thereof. In another embodiment, the solvent is selected from the group consisting of a non-polar aprotic organic solvent and a polar aprotic organic solvent, or a mixture thereof. In another embodiment, the solvent is a non-polar organic solvent. In another embodiment, the solvent is a non-polar aprotic organic solvent. In another embodiment, the solvent is selected form the group consisting of diethyl ether and methyl tert-butyl ether, or a mixture thereof. In another embodiment, the solvent is diethyl ether. In another embodiment, the solvent is a polar organic solvent. In another embodiment, the solvent is a polar aprotic organic solvent. In another embodiment, the solvent is selected from the group consisting of tetrahydrofuran, dioxane, and DMSO, or a mixture thereof. In another embodiment, the solvent is tetrahydrofuran.

Another aspect of the present disclosure is directed to a process for preparing a compound having Formula III:

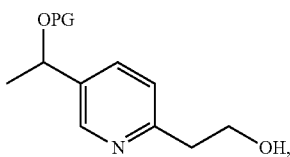

III the process comprising:
(a) reacting a compound having Formula II:

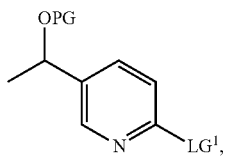

II with an alkyl lithium in a first solvent at a temperature to give a first reaction mixture;
wherein:
the temperature is below −20° C.:
PG is a protecting group, e.g., a protected group selected from the group consisting of a silyl protecting group, tetrahydropyranyl, methoxymethyl, and benzyl; and
$LG^1$ is a leaving group, e.g., —Br,
(b) adding a solution of ethylene oxide in a second solvent at said temperature to said first reaction mixture at said temperature to give a second reaction mixture; and
(c) adding a copper(I)salt, e.g., copper(I)iodide, or a Lewis acid, e.g., $BF_3.O(Et)_2$, $BBr_3$, or $BCl_3$, to said second reaction mixture at said temperature to give a third reaction mixture comprising a compound having Formula III.

Another aspect of the present disclosure is directed to a process for preparing a compound having Formula III:

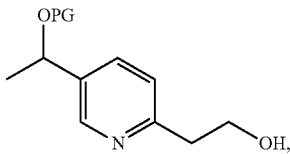

III the process comprising:
(a) reacting a compound having Formula II:

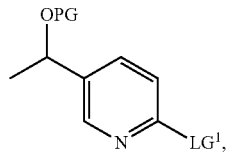

II with an alkyl lithium in a first solvent at a temperature to give a first reaction mixture;
wherein:
the temperature is below −20° C.;
PG is a protecting group, e.g., a protecting group selected from the group consisting of a silyl protecting group, tetrahydropyranyl, methoxymethyl, and benzyl; and
$LG^1$ is a leaving group, e.g. —Br,
(b) adding a copper(I)salt, e.g., copper(I)iodide, or a Lewis acid, e.g., $BF_3.O(Et)_2$, $BBr_7$, or $BCl_3$, to the first reaction mixture at said temperature to give a second reaction mixture; and
(c) adding a solution of ethylene oxide in a second solvent at said temperature to the second reaction mixture at said temperature to give a third reaction mixture comprising a compound having Formula III.

In one embodiment of these aspects of the disclosure, the temperature is below −55° C. In another embodiment, the third reaction mixture is allowed to warm to a temperature of 20° C.-25° C. In another embodiment, the third reaction mixture is kept at 20° C.-25° C. for at least 4 hours. In another embodiment, the third reaction mixture is kept at 20° C.-25° C. for at least 6 hours. In another embodiment, the reaction mixture is kept at 20° C.-25° C. for at least 8 hours. In another embodiment, the third reaction mixture is kept at 20° C.-25° C. for at least 10 hours. In another embodiment, the first solvent and the second solvent are each independently selected from the group consisting of a non-polar aprotic solvent and a polar aprotic solvent, or a mixture thereof. In another embodiment, the solvent is selected from the group consisting of diethyl ether, methyl tert-butyl ether, tetrahydrofuran, dioxane, and DMSO, or a mixture thereof. In one embodiment, the first solvent and the second solvent are different. In another embodiment, the first solvent and the second solvent are the same, such as, for example, diethyl ether.

Another aspect of the present disclosure is directed to a process, comprising combining the reactants:
(a) ethylene oxide;
(b) a compound having Formula II:

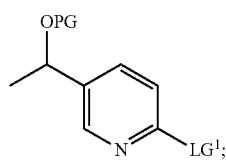

II (c) an alkyl lithium; and
(c) a copper(I)salt, e.g., copper(I)iodide, or a Lewis acid, e.g., $BF_3.O(Et)_2$, $BBr_3$, or $BCl_3$,
in a solvent at a temperature below −20° C., wherein:

PG is a protecting group, e.g., a protecting group selected from the group consisting of a silyl protecting group, tetrahydropyranyl, methoxymethyl, and benzyl; and LG$^1$ is a leaving group e.g., —Br, to give a compound having Formula III:

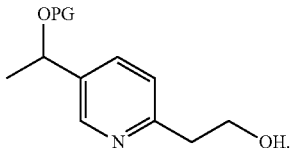

III

In one embodiment of this aspect of the invention, the reactants are combined in a solvent at below −55° C. In one embodiment, the alkyl lithium is added to a solution of the compound having Formula II in the solvent at the temperature to form a first reaction mixture. In another embodiment, a solution of the ethylene oxide in the solvent is cooled to the temperature and added to the first reaction mixture at the temperature to give a second reaction mixture. In one embodiment, the solvent is selected from the group consisting of a non-polar organic solvent and a polar organic solvent, or a mixture thereof. In another embodiment, the solvent is selected from the group consisting of a non-polar aprotic organic solvent and a polar aprotic organic solvent, or a mixture thereof. In another embodiment, the solvent is a non-polar organic solvent. In another embodiment, the solvent is a non-polar aprotic organic solvent. In another embodiment, the solvent is diethylether or tert-butyl methyl ether. In another embodiment, the solvent is a polar organic solvent. In another embodiment, the solvent is a polar aprotic organic solvent. In another embodiment, the solvent is selected from the group consisting of tetrahydrofuran, dioxane, and DMSO, or a mixture thereof.

In one embodiment, the copper(I)salt, e.g., copper(I) iodide, or Lewis acid, e.g., BF$_3$.O(Et)$_2$, BBr$_3$, or BCl$_3$, is added to the second reaction mixture at the temperature to give a third reaction mixture. In another embodiment, copper(I)iodide is added to the second reaction mixture at the temperature to give a third reaction mixture. In another embodiment, the third reaction mixture is allowed to warm to a temperature of 20° C.-25° C. In another embodiment, the third reaction mixture is kept at 20° C.-25° C. for at least 4 hours, for at least 6 hours, for at least 8 hours, or for at least 10 hours.

In another embodiment, the copper(I)salt, e.g., copper(I) iodide, or the Lewis acid, e.g., BF$_3$.O(Et)$_2$, BBr$_3$, or BCl$_3$, is added to the first reaction mixture at the temperature to give a fourth reaction mixture. In another embodiment, copper(I)iodide is added to the first reaction mixture at the temperature to give a fourth reaction mixture. In another embodiment, a solution of the ethylene oxide in the solvent is cooled to the temperature and added to the fourth reaction mixture at the temperature to give a fifth reaction mixture. In another embodiment, the fifth reaction mixture is allowed to warm to a temperature of 20° C.-25° C. In another embodiment, the reaction mixture is kept at 20° C.-25° C. for at least 4 hours. In another embodiment, the reaction mixture is kept at 20° C.-25° C. for at least 6 hours. In another embodiment, the reaction mixture is kept at 20° C.-25° C. for at least 8 hours. In another embodiment, the reaction mixture is kept at 20° C.-25° C. for at least 10 hours.

Another aspect of the present disclosure is directed to a process for preparing an intermediate having Formula III:

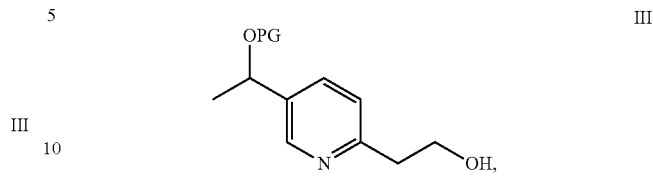

III wherein PG is a protecting group selected from the group consisting of a silyl protecting group, tetrahydropyranyl, or methoxymethyl, said process comprising reacting a compound of Formula II:

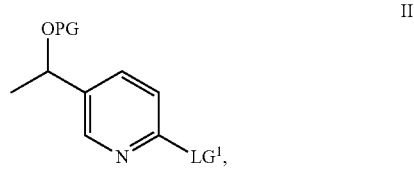

II wherein PG is as defined above and LG$^1$ is a leaving group, with ethylene oxide in the presence of (a) an alkyl lithium and copper(I)iodide or (b) an alkyl lithium and a Lewis acid selected from the group consisting of BF$_3$.O(Et)$_2$ (boron trifluoride etherate), BBr$_3$ and BCl$_3$, and a solvent, wherein the reaction temperature is maintained below −20° C. to give the compound of Formula III. Preferably, PG is selected from a silyl protecting group.

In another embodiment, the process further comprises isolating said compound of Formula III and optionally purifying the isolated compound of Formula III.

Another aspect of the disclosure is drawn to a process for preparing a compound of Formula IV:

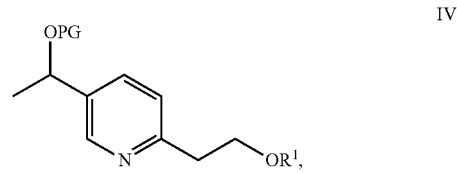

IV comprising reacting the compound of Formula III:

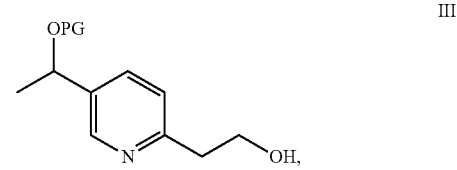

III wherein PG is as defined above, with R$^1$—Cl, wherein R$^1$ is an organosulfonate, in the presence of a first base.

In another aspect, the disclosure is drawn to a process of preparing a compound of Formula V:

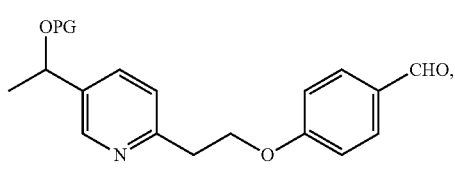

V wherein PG is as defined above, comprising reacting the compound of Formula IV with 4-hydroxybenzaldehyde having the structure

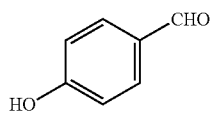

in the presence of a second base, such as an alkali metal carbonate, and optionally a solvent.

In another aspect, the disclosure is drawn to a process of preparing a compound of Formula VI:

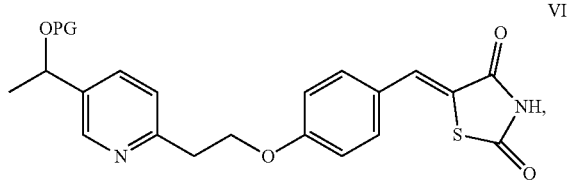

VI wherein PG is as defined above, comprising reacting the compound of Formula V with 2,4-thiazolidinedione of formula

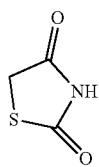

in the presence of piperidine and optionally a solvent, such as an alcohol, and optionally an organic acid. Preferably, this reaction in conducted in the presence of piperidine and a solvent, and optionally an organic acid.

In another aspect, the disclosure is directed to a process of preparing a compound of Formula VII:

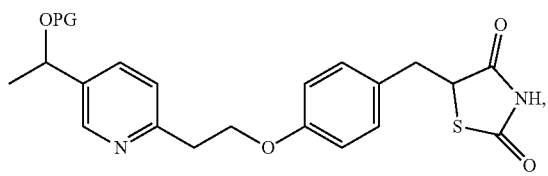

VII wherein PG is as defined above, comprising reducing the compound of Formula VI.

In another aspect, the disclosure is directed to a process for preparing a compound of Formula I:

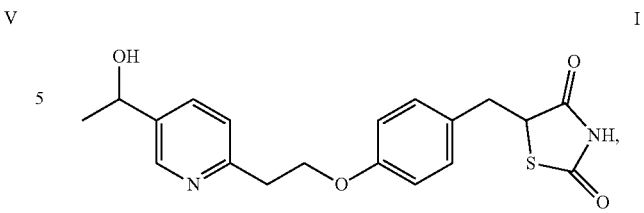

I or a pharmaceutically acceptable salt thereof, comprising de-protecting the compound of Formula VII and optionally further treating with an acid to form a salt.

In one embodiment, the process further comprises isolating said compound of Formula I, or a pharmaceutically acceptable salt thereof, and optionally purifying the isolated compound of Formula I, or a pharmaceutically acceptable salt thereof. In another embodiment, the process further comprises precipitating the compound of Formula I, or a pharmaceutically acceptable salt thereof. In one embodiment, the precipitation is conducted by treating the reaction mixture with a polar aprotic solvent, such as acetonitrile, at an elevated temperature, such as at reflux temperature, and then allowing the reaction mixture to cool to room temperature. In another embodiment, the process further comprises isolating the precipitate comprising the compound of Formula I, or a pharmaceutically acceptable salt thereof. In one embodiment, the precipitate is isolated by filtration. In another embodiment, the isolated precipitate is further purified by, e.g., washing with the solvent used in the precipitation or an aqueous mixture thereof.

In another embodiment, the process further comprises deuterating the compound of Formula I, or a pharmaceutically acceptable salt thereof. In another embodiment, the isolated compound of Formula I, or a pharmaceutically acceptable salt thereof, is deuterated.

In another aspect, the disclosure is directed to a compound of Formula III obtained by a process described herein by reacting the compound of Formula II.

In another aspect, the disclosure is directed to a compound of Formula I obtained by any process described herein.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

A number of attempts have been made by the inventors to find a route for synthesizing 5-[[4-[2-[5-(1-hydroxyethyl)-2-pyridinyl]ethoxy]phenyl]methyl]-2,4-thiazolidinedione, as well as the intermediate of Formula III as defined below, in a commercial scale, obtaining an improved overall yield of 5-[[4-[2-[5-(l-hydroxyethyl)-2-pyridinyl]ethoxy]phenyl] methyl]-2,4-thiazolidinedione. It has now been discovered that Compounds of the Disclosure can be synthetized in a simple process applicable for large scale and affording the product in a high purity and an improved overall yield.

The present disclosure provides a process for preparing the synthetic intermediate of Formula III having the structure:

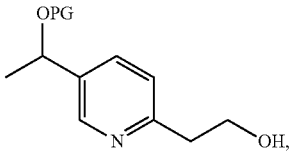

III wherein PG is a protecting group, said process comprises reacting a compound of Formula II:

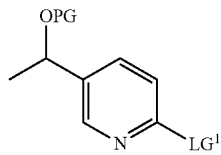

II wherein PG is a protecting group and $LG^1$ is a leaving group,
with ethylene oxide in the presence of
(a) an alkyl lithium and a copper(I)salt, or
(b) an alkyl lithium and a Lewis acid, and
a solvent,
to give a compound of Formula III:

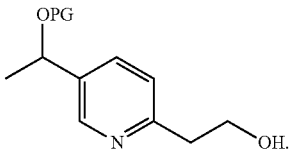

III

In one embodiment, PG is a silyl protecting group, tetrahydropyranyl, methoxymethyl, or benzyl. In another embodiment, PG is silyl protecting group, tetrahydropyranyl, or methoxymethyl. In another embodiment, PG is a silyl protecting group.

In one embodiment, the copper(I)salt is selected from the group consisting of copper(I)bromide, copper(I)chloride, and copper(I)iodide. In another embodiment, the copper(I) salt is copper(I)iodide.

In another embodiment, the Lewis acid is selected from the group consisting of $AlBr_3$, $AlCl_3$, $FeBr_3$, $FeCl_3$, $SnCl_4$, $Ti(OiPr)_4$, $BF_3$, $BF_3.O(Et)_2$, $BBr_3$, $BCl_3$, $TiCl_4$, and $ZnCl_2$. In another embodiment, the Lewis acid is selected from the group consisting of $BF_3.O(Et)_2$, $BBr_3$, $BCl_3$, $TiCl_4$, and $ZnCl_2$. In another embodiment, the Lewis acid is selected from the group consisting of $BF_3.O(Et)_2$, $BBr_3$ and $BCl_3$.

In another embodiment, the leaving group ($LG^1$) is —Br.

In another embodiment, the process comprises an alkyl lithium and copper(I)iodide.

The present disclosure provides a process for preparing the synthetic intermediate of Formula III having the structure:

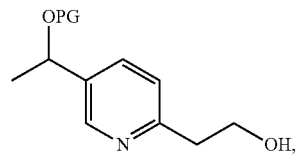

III wherein PG is a protecting group, said process comprises reacting a compound of Formula II:

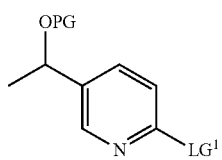

II wherein PG is a protecting group and $LG^1$ is a leaving group,
with ethylene oxide in the presence of
(a) an alkyl lithium and a copper(I) salt, e.g., copper(I) iodide; or
(b) an alkyl lithium and a Lewis acid, e.g., $BF_3.O(Et)_2$, $BBr_3$ or $BCl_3$, and
a solvent,
to give a compound of Formula III:

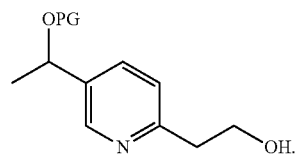

III

In another embodiment, PG is a protecting group selected from the group consisting of a silyl protecting group, tetrahydropyranyl, methoxymethyl, and benzyl. In another embodiment, PG is a protecting group selected from the group consisting of a silyl protecting group, tetrahydropyranyl, and methoxymethyl.

In one embodiment, the reagents, i.e., the ethylene oxide, alkyl lithium, and copper(I)salt, e.g., copper(I)iodide, or the Lewis acid, are added into the reaction mixture comprising the compound of Formula II at low temperature, e.g., at a temperature of about −20° C., about −25° C., about −30° C., about −35° C., about −40° C., about −45° C., about −50° C., about −55° C., about −60° C., about −65° C., about −70° C., or about −75° C. In another embodiment, the reagents are added while maintaining the temperature of the reaction mixture below −20° C. In another embodiment, the reagents are added while maintaining the temperature of the reaction mixture at about <−55° C. In another embodiment, the reagents are added to the reaction mixture at about <−55° C.

In another embodiment, the ethylene oxide is added into the reaction mixture after first adding the alkyl lithium. In another embodiment, the ethylene oxide is added into the reaction mixture after adding the alkyl lithium and the copper(I)salt, e.g., copper(I)iodide, or the Lewis acid. In another embodiment, the reaction mixture is allowed to warm to room temperature, e.g., about 20-25° C., after the addition of the reagents. In another embodiment, the reaction mixture is kept at 20° C.-25° C. for at least 4 hours, for at least 6 hours, or for at least 8 hours. In another embodiment, the reaction mixture is kept at 20° C.-25° C. for at least 10 hours.

In one embodiment of this aspect of the disclosure, the reaction is conducted in the presence of an alkyl lithium and a copper(I)salt. In another embodiment, the reaction is conducted in the presence of an alkyl lithium and copper(I) iodide. In another embodiment, the reaction is conducted in the presence of an alkyl lithium and a Lewis acid. In another embodiment, the reaction is conducted in the presence of an alkyl lithium and a Lewis acid selected from the group consisting of $BF_3.O(Et)_2$, $BBr_3$ and $BCl_3$.

In another embodiment, the process of the disclosure comprises reacting a compound of Formula II:

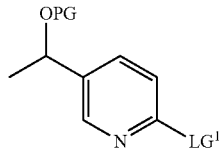

wherein PG is a protecting group selected from the group consisting of a silyl protecting group, tetrahydropyranyl, and methoxymethyl, and
$LG^1$ is a leaving group,
with ethylene oxide in the presence of an alkyl lithium and copper(I)iodide, and
a solvent, wherein
the reaction temperature is maintained below −20° C. when adding the alkyl lithium and the copper(I)iodide into the reaction mixture,
to give a compound of Formula III:

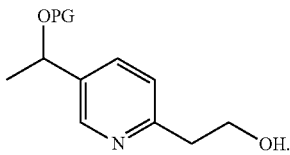

In one embodiment, the ethylene oxide is added into the reaction mixture after first adding the alkyl lithium. In another embodiment, the ethylene oxide is added to the reaction mixture while maintaining the reaction temperature below −20° C. In another embodiment, the alkyl lithium and copper(I)salt, e.g., copper(I)iodide are added while maintaining the temperature of the reaction mixture below −55° C. In another embodiment, the ethylene oxide is added to the reaction mixture while maintaining the reaction temperature below −55° C. In another embodiment, the reaction mixture is allowed to warm to room temperature, e.g., about 20-25° C., after the addition of the reagents. In another embodiment, the reaction mixture is kept at 20° C.-25° C. for at least 4 hours, for at least 6 hours, or for at least 8 hours. In another embodiment, the reaction mixture is kept at 20° C.-25° C. for at least 10 hours.

In one embodiment, the solvent is selected from the group consisting of a non-polar organic solvent and a polar organic solvent, or a mixture thereof. In another embodiment, the solvent is selected from the group consisting of a non-polar aprotic organic solvent and a polar aprotic organic solvent, or a mixture thereof. In another embodiment, the solvent is a non-polar organic solvent. In another embodiment, the solvent is a non-polar aprotic organic solvent. In another embodiment, the solvent is diethyl ether or methyl tert-butyl ether. In another embodiment, the solvent is a polar organic solvent. In another embodiment, the solvent is a polar aprotic organic solvent. In another embodiment, the solvent is selected from the group consisting of tetrahydrofuran, dioxane, and DMSO, or a mixture thereof.

In another embodiment, the process of the disclosure provides a process for preparing a compound having Formula III:

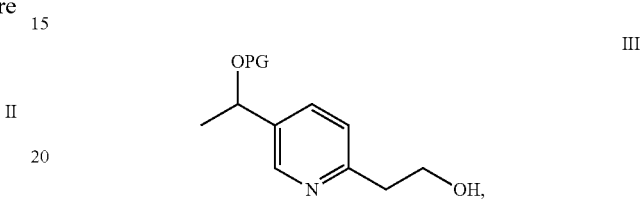

the process comprising:
(a) reacting a compound having Formula II:

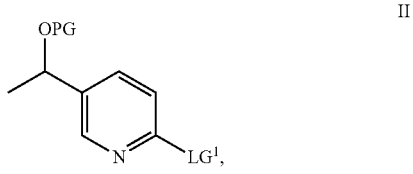

with an alkyl lithium in a first solvent at a temperature to give a first reaction mixture;
wherein:
the temperature is below −20° C.;
PG is a protecting group, e.g., a protecting group selected from the group consisting of a silyl protecting group, tetrahydropyranyl, methoxymethyl, and benzyl; and
$LG^1$ is a leaving group, e.g., Br;
(b) adding a solution of ethylene oxide in a second solvent at said temperature to said first reaction mixture at said temperature to give a second reaction mixture; and
(c) adding a copper(I)salt, e.g., copper(I)iodide, or a Lewis acid, e.g., $BF_3.O(Et)_2$, $BBr_3$, or $BCl_3$, to said second reaction mixture at said temperature to give a third reaction mixture comprising a compound having Formula III.

In another embodiment, the process of the disclosure provides a process for preparing a compound having Formula III:

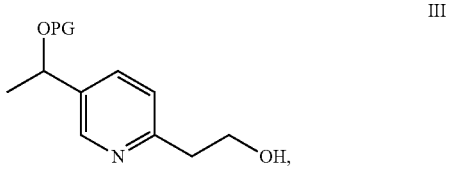

the process comprising:
(a) reacting a compound having Formula II:

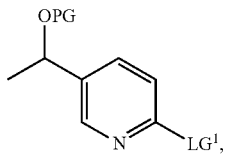

with an alkyl lithium in a first solvent at a temperature to give a first reaction mixture,
wherein:
the temperature is below −20° C.;
PG is a protecting group, e.g., a protecting group selected from the group consisting of a silyl protecting group, tetrahydropyranyl, and methoxymethyl; and
LG$^1$ is a leaving group,
(b) adding a copper(I)salt, e.g., copper(I)iodide, or a Lewis acid, e.g., BF$_3$.O(Et)$_2$, BBr$_3$, or BCl$_3$, to the first reaction mixture at said temperature to give a second reaction mixture; and
(c) adding a solution of ethylene oxide in a second solvent at said temperature to the second reaction mixture at said temperature to give a third reaction mixture comprising a compound having Formula III.

In one embodiment of these aspects of the disclosure, the temperature is below −55° C. In another embodiment, the third reaction mixture is allowed to warm to a temperature of 20° C.-25° C. In another embodiment, the third reaction mixture is kept at 20° C.-25° C. for at least 4 hours. In another embodiment, the third reaction mixture is kept at 20° C.-25° C. for at least 6 hours. In another embodiment, the reaction mixture is kept at 20° C.-25° C. for at least 8 hours. In another embodiment, the third reaction mixture is kept at 20° C.-25° C. for at least 10 hours. In one embodiment, the first solvent and the second solvent are different. In another embodiment, the first solvent and the second solvent are the same, such as, for example, diethyl ether. Suitable solvents are those described above. In another embodiment, LG$^1$ is bromide, i.e., —Br.

In another embodiment, the first solvent is selected from the group consisting of a non-polar aprotic solvent and a polar aprotic solvent, or a mixture thereof. In one embodiment, the first solvent is a non-polar aprotic solvent. In another embodiment, the first solvent is selected from the group consisting of diethyl ether and methyl tert-butyl ether, or a mixture thereof. In another one embodiment, the first solvent is a polar aprotic solvent. In another embodiment, the first solvent is selected from the group consisting of THF, dioxane, and DMSO, or a mixture thereof.

In another embodiment, the second solvent is selected from the group consisting of a non-polar aprotic solvent and a polar aprotic solvent, or a mixture thereof. In one embodiment, the second solvent is a non-polar aprotic solvent. In another embodiment, the second solvent is selected from the group consisting of diethyl ether and methyl tert-butyl ether, or a mixture thereof. In another one embodiment, the second solvent is a polar aprotic solvent. In another embodiment, the second solvent is selected from the group consisting of THF, dioxane, DMSO, and a mixture thereof.

In another embodiment, the first solvent and the second solvent are each independently selected from the group consisting of a non-polar aprotic solvent and a polar aprotic solvent, or a mixture thereof. In another embodiment, the first solvent and the second solvent are different. In another embodiment, the first solvent and the second solvent are the same solvents. In another embodiment, both the first solvent and the second solvent are diethyl ether. In another embodiment, the process further comprises isolating the compound having Formula III.

In another embodiment, the process of the disclosure provides to a process, comprising
combining the reactants:
(a) ethylene oxide;
(b) a compound having Formula II:

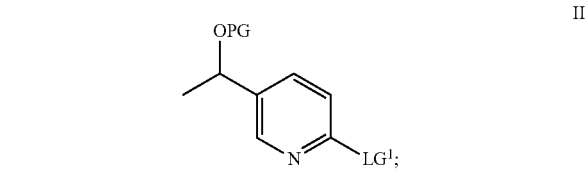

(c) an alkyl lithium; and
(d) a copper(I) salt, e.g., copper(I)iodide, or a Lewis acid, e.g., BF$_3$.O(Et)$_2$, BBr$_3$, or BCl$_3$,
in a solvent at a temperature below −20° C.,
wherein:
PG is a protecting group, e.g., a protecting group selected from the group consisting of a silyl protecting group, tetrahydropyranyl, methoxymethyl, and benzyl; and
LG$^1$ is a leaving group,
to give a compound having Formula III:

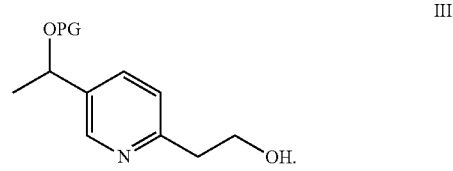

The term "reactant" or "reagent" as used herein refers to a substance that takes part in and/or undergoes change during a chemical reaction.

In the processes described herein, reactants can be combined in any order that provides Formula III in an acceptable yield and purity. Reactants can also be combined as is or as a solution. For example, a solvent can be added to ethylene oxide to form a solution, and this solution can be added to another reactant.

In one embodiment of this aspect of the invention, the reactants are combined in a solvent below −55° C. In one embodiment, the alkyl lithium is added to a solution of the compound having Formula II in the solvent at the temperature to form a first reaction mixture. In another embodiment, a solution of the ethylene oxide in the solvent is cooled to the temperature and added to the first reaction mixture at the temperature to give a second reaction mixture. In one embodiment, the solvent is selected from the group consisting of a non-polar aprotic organic solvent and a polar aprotic organic solvent, or a mixture thereof. In another embodiment, the solvent is a non-polar aprotic organic solvent. In another embodiment, the solvent is selected from the group consisting of diethyl ether and methyl tert-butyl ether, or a mixture thereof. In another embodiment, the solvent is a polar aprotic organic solvent. In another embodiment, the solvent is selected from the group consisting of tetrahydrofuran, dioxane, and DMSO, or a mixture thereof.

In one embodiment, the copper(I)salt, e.g., copper(I) iodide, or Lewis acid, e.g., $BF_3.O(Et)_2$, $BBr_3$, or $BCl_3$, is added to the second reaction mixture at the temperature to give a third reaction mixture. In another embodiment, copper(I)iodide is added to the second reaction mixture at the temperature to give a third reaction mixture. In another embodiment, the third reaction mixture is allowed to warm to a temperature of 20° C.-25° C. In another embodiment, the third reaction mixture is kept at 20° C.-25° C. for at least 4 hours. In another embodiment, the third reaction mixture is kept at 20° C.-25° C. for at least 6 hours. In another embodiment, the third reaction mixture is kept at 20° C.-25° C. for at least 8 hours. In another embodiment, the third reaction mixture is kept at 20° C.-25° C. for at least 10 hours.

In another embodiment, the copper(I)salt, e.g., copper(I) iodide, or the Lewis acid, e.g., $BF_3.O(Et)_2$, $BBr_3$, or $BCl_3$ is added to the first reaction mixture at the temperature to give a fourth reaction mixture. In another embodiment, copper (I)iodide is added to the first reaction mixture at the temperature to give a fourth reaction mixture. In another embodiment, a solution of the ethylene oxide in the solvent is cooled to the temperature and added to the fourth reaction mixture at the temperature to give a fifth reaction mixture. In another embodiment, the fifth reaction mixture is allowed to warm to a temperature of 20° C.-25° C. In another embodiment, the fifth reaction mixture is kept at 20° C.-25° C. for at least 4 hours. In another embodiment, the fifth reaction mixture is kept at 20° C.-25° C. for at least 6 hours. In another embodiment, the fifth reaction mixture is kept at 20° C.-25° C. for at least 8 hours. In another embodiment, the fifth reaction mixture is kept at 20° C.-25° C. for at least 10 hours. In another embodiment, $LG^1$ is —Br.

In another embodiment, the present disclosure provides a process for preparing the key intermediate used in the process of preparing Compounds of the Disclosure, having Formula III:

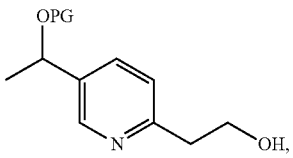

III wherein PG is a protecting group selected from silyl protecting groups, tetrahydropyranyl, or methoxymethyl, said process comprising reacting a compound of Formula II having the structure:

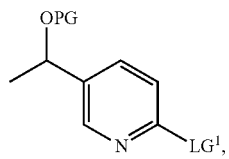

II wherein PG is a as defined above and $LG^1$ is a leaving group, with ethylene oxide in the presence of (a) an alkyl lithium and copper(I)iodide or (b) an alkyl lithium and a Lewis acid selected from the group consisting of $BF_3.O(Et)_2$, $BBr_3$ and $BCl_3$, and a solvent, wherein the reaction temperature is maintained below −20° C. to give the compound of Formula III.

In one embodiment, PG is selected from silyl protecting groups. In another embodiment, PG is an alkyl or aryl silyl group, or a combination thereof. In another embodiment, PG is a trialkylsilyl group. In another embodiment, PG is selected from the group consisting of tert-butyldimethylsilyl (TBDMS), trimethylsilyl (TMS), triethylsilyl (TES), tert-butyldiphenylsilyl (TBDPS), and triisopropylsilyl (TIPS). In another embodiment, PG is tert-butyldimethylsilyl (TBDMS).

In another embodiment, PG is tetrahydropyranyl. In another embodiment, PG is methoxymethyl. In another embodiment, PG is benzyl. Preferably, PG is a silyl protecting group.

Suitable leaving groups for $LG^1$ include chloride (—Cl), bromide (—Br), iodide (—I), and fluoride (—F). Preferably, $LG^1$ is bromide.

The solvent used in this reaction can be a non-polar or polar organic solvent. In one embodiment, the solvent is a non-polar or polar aprotic organic solvent. In one embodiment, the solvent is a non-polar aprotic solvent selected from ethers, such as, for example, diethylether and methyl tert-butyl ether. In another embodiment, the solvent is a polar aprotic solvent, such as, for example, tetrahydrofuran (THF). In another embodiment, the polar aprotic solvent is dioxane or dimethyl sulfoxide (DMSO).

In one embodiment, the reaction is conducted in the presence of an alkyl lithium and a copper(I)salt, e.g., copper (I)iodide, copper(I)bromide, or copper(I)chloride. In another embodiment, the reaction is conducted in the presence of an alkyl lithium and copper(I)iodide. In another embodiment, the alkyl lithium is $C_{1-6}$ alkyl lithium. In another embodiment, the alkyl lithium is selected from the group consisting of n-butyllithium (n-BuLi), sec-butyllithium (sec-BuLi), and hexyllithium (HxLi). A suitable molar ratio of the alkyl lithium and copper(I)iodide used in the reaction is from about 8:1 to about 2:1. In one embodiment, the molar ratio of the alkyl lithium and copper(I)iodide is about 2:1. In one embodiment, the complexed copper is removed after the reaction by washing with 10% ammonia.

In another embodiment, the reaction is conducted in the presence of an alkyl lithium and a Lewis acid. In another embodiment, the reaction is conducted in the presence of an alkyl lithium and a Lewis acid selected from the group consisting of $BF_3.O(Et)_2$, $BBr_3$ and $BCl_3$. In another embodiment, the Lewis acid is $BF_3.O(Et)_2$. Suitable alkyl lithium compounds are described above.

In one embodiment, the reaction temperature, i.e., the temperature of the reaction mixture, to form the compound of Formula III is maintained at low temperatures, such as from about −20° C. to about −85° C., when adding the reagents into the reaction mixture comprising the compound od Formula II, followed by stirring at room temperature, e.g., about 20-25° C. In another embodiment, the addition to the reaction mixture is conducted at a temperature of from about −40° C. to about −70° C. In another embodiment, the addition to the reaction mixture is conducted at a temperature of from about −50° C. to about −65° C. In another embodiment, the reaction temperature is maintained below about −55° C. when adding the reagents In one embodiment, the reaction time to form the compound of Formula III from a compound of Formula II is at least 24 hours. In another embodiment, the reaction times to form the compound of Formula III from a compound of Formula II are from about 24 to about 40 hours, or about 27 hours, or about 30 hours, or about 36 hours.

After the reaction to form the compound of Formula III from the compound of Formula II is complete, the compound of Formula III is isolated from the reaction mixture and preferably purified, for example, by column chromatography or re-crystallization, and preferably by column chromatography, such as HPLC. The compound of Formula III can be obtained in a good yield with high purity. In certain aspects of the disclosure, the inventors have obtained the compound of Formula III using the process described above at about 95% yield and about 80% purity. In certain aspects of the disclosure, the inventors have obtained the compound of Formula III using the process described above at about 50% yield and about 99% purity.

The process of the disclosure further comprises reacting the compound of Formula III with $R^1$—Cl, wherein $R^1$ is an organosulfonate, such as a tosyl group (Ts) or a mesyl group (Ms), in the presence of a first base to give a compound of Formula IV:

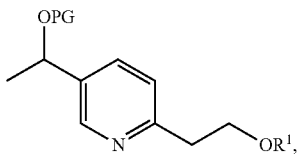

IV wherein PG and $R^1$ are as defined above. The first base can be, for example, one or more of an amine, a quaternary ammonium salt in combination with a water solution of an alkalimetal hydroxide, tetrabutylammoniumhydroxide, or an alkalimetal hydroxide. In one embodiment, the first base is an amine. Suitable amines include, for example, trialkylamine, such as triethylamine, and pyridine. In another embodiment, the first base is a quaternary ammonium salt, such as tetra-n-butylammonium bromide or tetra-n-butylammonium fluoride in combination with a water solution of an alkalimetal hydroxide. Suitable alkalimetal hydroxides include NaOH and KOH. In another embodiment, the first base is tetrabutylammoniumhydroxide. In another embodiment, the first base is tetra-n-butylammonium bromide in aqueous alkalimetal hydroxide solution. In another embodiment, the first base is tetra-n-butylammonium bromide in 30% NaOH.

In another embodiment, $R^1$—Cl is used in an amount of from about 1 equivalent to about 1,50 equivalents. In another embodiment, $R^1$—Cl is p-Ts-Cl in an amount of from 1 equivalent to about 1,1 equivalents.

Advantageously, the reaction to prepare the compound of Formula IV is conducted in the presence of a solvent, such as, for example, toluene or DCM. In one embodiment, the solvent is toluene.

In another embodiment, the reaction to prepare the compound of Formula IV is obtained by reacting p-Ts-Cl (about 1 eq to about 1.1 eq) with the compound of Formula III in the presence of toluene, 30% aqueous NaOH and tetra-n-butylammonium bromide.

In one embodiment, the reaction for preparing the compound of Formula IV is conducted at a temperature of from about 15° C. to about 30° C., and preferably at a temperature of from about 20° C. to about 25° C., and preferably at about 20° C.

In one embodiment, the reaction times to form the compound of Formula IV from the compound of Formula III are from about 5 to about 26 hours, or from about 10 to about 26, or from about 15 to about 25 hours, or about 22 hours.

The process of the disclosure further comprises reacting the compound of Formula IV with 4-hydroxybenzaldehyde:

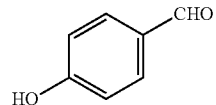

in the presence of a second base and a solvent to give a compound of Formula V

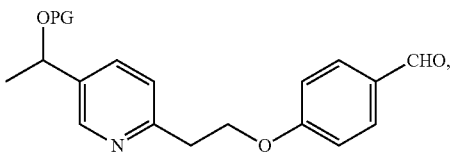

V wherein PG is as defined above. Suitable second bases include, for example, alkali metal carbonates (such as potassium carbonate ($K_2CO_3$)), trialkylamines (such as triethylamine ($Et_3N$)), and alkali metal alkoxides (such as potassium tert-butoxide (KOtBu)). In one embodiment, the second base is $K_2CO_3$. Advantageously, the amount of the second base is from about 1 eq to about 2 eq, and preferably about 1 eq.

In one embodiment, the solvent is selected from the group consisting of toluene, ethanol, 2-propanol, THF, 2-MeTHF, and water, or combinations thereof. In another embodiment, the solvent is a mixture of toluene and ethanol. In another embodiment, the solvent is a mixture of toluene and ethanol in a ratio of about 6:4.

In one embodiment, the reaction for preparing the compound of Formula V is conducted at a temperature of from about 50° C. to about 80° C., and preferably at about 80° C.

In one embodiment, additional water is added to the reaction mixture. In one embodiment, the amount of water added is from about 2% to about 7% v/v (i.e., the volume of water relative to the volume of solvents used). In another embodiment, water is added in an amount of about 4% v/v, about 5% v/v, or about 6% v/v. In another embodiment, water is added in an amount of 5% v/v. In another embodiment, the temperature of the reaction is mixture is from about 20° C. to about 30° C. In another embodiment, water is added at about 20° C.

In one embodiment, the reaction times to form the compound of Formula V from the compound of Formula IV are from about 6 to about 24 hours, or from about 10 to about 22 hours, or about 16 hours, or about 18 hours.

In another embodiment, the process comprises isolating and purifying the compound of Formula V. In one embodiment, the purifying is performed by extraction. In another embodiment, the purifying comprises extracting with an aqueous bisulfite solution. In another embodiment, the purifying comprises extracting a solution comprising the compound of Formula V and ethanol with an aqueous bisulfite solution comprising ethanol; separating the aqueous phase; extracting the aqueous phase with a mixture of toluene and heptane wherein the pH of the mixture is adjusted to pH 12:separating the organic layer; and recovering said purified compound of Formula V. In one embodiment, the pH is adjusted to pH 12 by addition of aqueous NaOH.

The process of the present disclosure further comprises reacting the compound of Formula V with 2,4-thiazolidinedione:

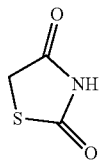

in the presence of piperidine and optionally a solvent, and optionally an organic acid, to give a compound of Formula VI:

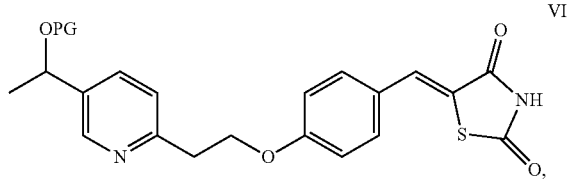

wherein PG is as defined above.

In one embodiment, the reaction to form a compound of Formula VI is carried out in the presence of piperidine and a solvent, and optionally an organic acid. Suitable solvents in this reaction include toluene, lower alcohols (such as methanol and ethanol), hexane, cyclohexane, and mixtures thereof. In one aspect, the solvent is toluene or methanol, or a mixture thereof. Advantageously, the solvent is methanol.

In one embodiment, the reaction is carried out in the presence of an organic acid. Suitable organic acids include carboxylic acids, such as, for example, ($C_{1-12}$)alkyl carboxylic acids (e.g., acetic acid), formic acid, and benzoic acid. In another embodiment, the reaction is carried out without an organic acid.

Suitable reaction temperatures for obtaining the compound of Formula VI depend on the solvent used in the reaction. For example, suitable reaction temperature can vary within the range of from about 45° C. to about 80° C. Preferably, the reaction temperature is about 47° C. when the solvent is methanol. Preferably, the reaction temperature is about 78° C. when the solvent is toluene. The reaction time varies depending on the solvent and can be from about 5 hours to about 37 hours, or from about 9 to about 25 hours.

In another embodiment, the reaction to form the compound of Formula VI is carried out in the absence of a solvent, at a temperature which is sufficiently high to cause at least partial melting of the reaction mixture. A preferred such temperature is in the range of from 100° C. to 250° C., and especially from 140° C. to 200° C.

Preferably, the reaction to form the compound of Formula VI is carried out in the presence of a solvent, and optionally an organic acid.

The process of the present disclosure further comprises reducing the compound of Formula VI to give a compound of Formula VII:

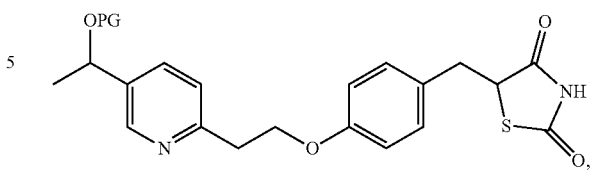

wherein PG is as defined above. The reduction is typically conducted by allowing the compound of Formula VI to react with a reducing agent in the presence of a metal ion and a complexing agent for the metal ion (a ligand).

The reaction temperature of this reduction reaction can vary between −20° C. and +45° C., and is preferably between +20° C. and +35° C. Advantageously, the reaction temperature is about +30° C.

Suitable solvents to be used in this reduction step include methanol, ethanol, i-propanol, dimethylformamide (DMF), and tetrahydrofuran (THF). If DMF or THF are used as solvents, water or an alcohol (such as methanol, ethanol or i-propanol) must be present (typically in an amount of ≥1 eq). Advantageously, the solvent combination contains water and THF. In one embodiment, the solvent combination contains an aqueous NaOH solution, a carboxylic acid (such as acetic acid), and THF.

In one embodiment, the pH of the reaction mixture is maintained at about pH 9.5 to about pH 10.5.

Suitable reducing agents include sodium borohydride ($NaB_4$), lithium borohydride, potassium borohydride, tetraalkylammonium borohydride and zinc borohydride. In one embodiment, the reducing agent is $NaBH_4$.

Preferably, the metal ion is cobalt ($Co^{+2}$ or $Co^{+3}$). Sources of cobalt include cobalt dichloride ($CoCl_2$), cobalt diacetate ($Co(OAc)_2$, and $CoCl_3$. Preferably, the metal ion is $Co^{2+}$.

Suitable ligands include dimethylglyoxime, 2,2'-bipyridyl, and 1,10-phenanthroline, and preferably dimethylglyoxime. The ligand should be used at least a 2:1 mole ratio with the cobalt ion, and preferably at a 50:1 ratio.

In another embodiment, the reduction is conducted under an inert atmosphere, such as, e.g., under a nitrogen atmosphere.

The process of the present disclosure further comprises deprotecting the compound of Formula VII, and optionally further treating with an acid, to give a compound of Formula I:

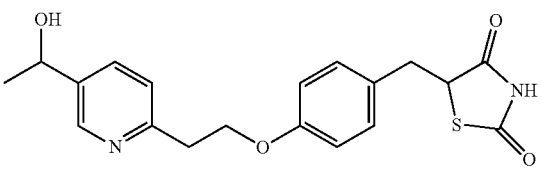

or a pharmaceutically acceptable salt thereof. The deprotection (i.e., the removal of the silyl ether protecting group) can be conducted in a suitable solvent by treating with acids or fluorides (e.g., tetra-n-butylammonium fluoride) as described, e.g., in Greene, T. W. and Wuts, P. G. M., Protective Groups in Organic Synthesis, p. 114 (J. Wiley & Sons, 1999). Subsequently, the deprotected compound of Formula I can be treated with a suitable acid (such as hydrochloric acid) to form the salt of the compound of Formula I.

In one embodiment, the deprotection of the compound of Formula VII and the salt formation are conducted in two separate steps as described above.

In another embodiment, the deprotection of the compound of Formula VII and the salt formation are simultaneous under the reaction conditions. The term "simultaneous" herein means that the deprotection and the salt formation happen at the same time or sequentially. For example, the compound of Formula I hydrochloric acid salt can be obtained simultaneously by treating the compound of Formula VII with 30% hydrochloric acid in methanol at an elevated temperature from about 35° C. to about 45° C., and preferably at about 40° C.

In one embodiment, the process further comprises isolating the compound of Formula I, or a pharmaceutically acceptable salt thereof, and optionally purifying the isolated compound of Formula I, or a pharmaceutically acceptable salt thereof.

In another embodiment, the process further comprises precipitating the compound of Formula I, or a pharmaceutically acceptable salt thereof. In one embodiment, the precipitating is conducted by treating the reaction mixture with a polar aprotic solvent, such as acetonitrile, at an elevated temperature, such as at reflux temperature, and then allowing the reaction mixture to cool to room temperature, e.g., 20-25° C. In another embodiment, the process further comprises isolating the precipitate comprising the compound of Formula I, or a pharmaceutically acceptable salt thereof, from the reaction mixture. In one embodiment, the precipitate is isolated by filtration. In another embodiment, the isolated precipitate is further purified by, e.g., washing with the solvent used in the precipitation and/or a mixture of the solvent and water. In another embodiment, the isolated precipitate is washed with acetonitrile and/or a mixture of acetonitrile and water, to obtain the isolated compound of Formula I, or a pharmaceutically acceptable salt thereof.

In another embodiment, the isolated compound of Formula I, or a pharmaceutically acceptable salt thereof, is further purified. In one embodiment, the isolated compound of Formula I, or a pharmaceutically acceptable salt thereof, is purified by dissolving the isolated compound in a suitable solvent (e.g., in aqueous methanol) and treating the solution with activated charcoal (e.g., a suspension in methanol) at an elevated temperature (e.g., at about 45° C.) for a sufficient time (e.g., 1 hour), filtering the activated charcoal, and then recovering the purified compound of Formula I, or a pharmaceutically acceptable salt thereof, from the filtrate.

The compound of Formula I, and pharmaceutically acceptable salts thereof, can be obtained in a good yield with high purity. In certain aspects of the disclosure, the inventors have obtained the compound of Formula I using the process described above at about 13% overall yield. In certain aspects of the disclosure, the inventors have obtained the compound of Formula I using the process described above at about 6% overall yield. As described above, the yield of the compound for Formula I depends on the yield and purity of the intermediate of Formula III.

In another embodiment, the process further comprises deuterating the compound of Formula I, or a pharmaceutically acceptable salt thereof. In another embodiment, the isolated compound of Formula I, or a pharmaceutically acceptable salt thereof, is deuterated. Methods known in the art can be used for preparing the deuterated compounds of Formula I, and the pharmaceutically acceptable salts thereof. For example, such methods are described in WO 2014/152843 A1.

In one embodiment of the present disclosure, the compound of Formula II is prepared by protecting the hydroxyl group of a compound of Formula VIII:

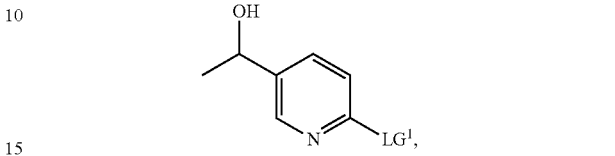

wherein $LG^1$ is a leaving group, as defined above, with PG, wherein PG is a protecting group, e.g., a protecting group selected from the group consisting of silyl protecting groups, tetrahydropyranyl, methoxymethyl, and benzyl. The protection of the hydroxyl group by a silyl protecting group, tetrahydropyranyl, methoxymethyl, or benzyl can be performed by methods known in the art. For example, if PG is a silyl protecting group, the compound of Formula VIII can be reacted with a silyl chloride (such as TBDMS-Cl, TMS-Cl, TBDPS-Cl, and TIPS-Cl) using an amine base (such as imidazole). One possible procedure is the Corey protocol in which the compound of Formula VIII is reacted with a silyl chloride and imidazole at high concentration in DMF.

In one embodiment of the present disclosure, the compound of Formula VIII is prepared by reacting a compound of Formula IX:

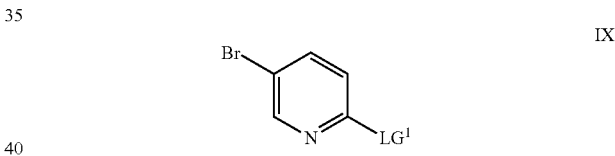

wherein $LG^1$ is a leaving group, as defined above, with $CH_3CHO$ in the presence of an alkylmagnesiumhalide in the presence of a solvent to give the compound of Formula VIII. Suitable alkylmagnesiumhalides include, for example, i-PrMgCl, t-BuMgCl, and t-BuMgBr. Compounds of Formula IX where $LG^1$ is a halogenide are also commercially available from, for example, OxChem Corporation. Suitable solvents include anhydrous ethereal solvents, such as THF and diethyl ether, and preferably THF.

The term "pharmaceutically acceptable salt" refers to a salt prepared from pharmaceutically acceptable inorganic and organic acids. Exemplary pharmaceutically acceptable acid addition salts of the Compounds of the Disclosure include, without limitation, hydrochloric, hydrobromic, hydroiodic, sulfuric, phosphoric, formic, acetic, trifluoroacetic, propionic, citric, and benzoic acids.

The term "hydroxyl protecting group" or a "protecting group" as used herein refers to group that blocks (i.e., protects) the hydroxy functionality while reactions are carried out on other functional groups or parts of the molecule. Those skilled in the art will be familiar with the selection, attachment, and cleavage of protecting groups and will appreciate that many different protective groups are known in the art, the suitability of one protective group or another being dependent on the particular synthetic scheme planned. Suitable hydroxyl protecting groups are generally able to be selectively introduced and removed using mild reaction conditions that do not interfere with other portions of the subject compounds. These protecting groups can be introduced or removed at a convenient stage using methods known in the art. The chemical properties of such groups, methods for their introduction and removal are known in the art and can be found, for example, in Wuts, P. G. M. & Greene, T. W., *Greene's Protective Groups in Organic Synthesis,* 4rd Ed., pp. 16-430 (J. Wiley & Sons, 2007), herein incorporated by reference in its entirety. Unless specifically specified, suitable hydroxyl protecting groups are disclosed in Wuts, P. G. M. & Greene, T. W., above. Additional hydroxyl protecting groups can be found, for example, in U.S. Pat. No. 5,952,495, U.S. Patent Appl. Pub. No. 2008/0312411, WO 2006/035195, and WO 98/02033, herein incorporated in their entirety. Suitable hydroxyl protecting groups include the methoxymethyl, tetrahydropyranyl, tert-butyl, allyl, tert-butyldimethylsilyl, tert-butyldiphenylsilyl, acetyl, pivaloyl, benzoyl, benzyl (Bn), and p-methoxybenzyl group.

The term "about," as used herein in connection with a measured quantity, refers to the normal variations in that measured quantity, as expected by the skilled artisan making the measurement and exercising a level of care commensurate with the objective of measurement and the precision of the measuring equipment.

Some of the compounds disclosed herein may contain one or more asymmetric centers and may thus give rise to enantiomers, diastereomers, and other stereoisomeric forms, such as epimers. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral stereogenic centers present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Open terms such as "include," "including," "contain," "containing" and the like mean "comprising."

The term "alkali metal" as used herein refers to sodium (Na), potassium (K), and lithium (Li). In one embodiment, the term "alkali metal" can also refer to cesium (Cs).

The term "carbonate" as used herein refers to a salt of carbonic acid characterized by the presence of the carbonate ion $CO_3^{2-}$.

The term "alkali metal carbonate" as used herein refers to a carbonate salt of any of the above mentioned alkali metals. Alkali metal carbonates include $K_2CO_3$, $Na_2CO_3$, $Li_2CO_3$, $KHCO_3$, and $NaHCO_3$.

The term "alkyl" as used herein by itself or as a part of another group refers to unsubstituted straight-chain, branched or cyclic aliphatic hydrocarbon containing from one to twelve carbon atoms, i.e., $C_{1-12}$ alkyl. In one embodiment, the alkyl group is $C_{1-6}$ alkyl. Exemplary $C_{1-6}$ alkyl groups include methyl, ethyl, propyl, iso-propyl, n-butyl, tert-butyl, sec-butyl, pentyl, hexyl, cyclopropyl, cyclobutyl, cyclopentyl and cyclohexyl.

The term "lower alkyl" refers to $C_{1-4}$ alkyl that is a straight-chain or branched-chain aliphatic hydrocarbon. Lower alkyl groups include methyl, ethyl, propyl, iso-propyl, n-butyl, sec-butyl, and tert-butyl.

The term "organosulfonate" as used herein refers to an organic anion $R-SO_3^-$, wherein R can be an organic group, such as methyl, ethyl, benzene, and p-toluene.

The term "silyl protecting groups" as used herein refers to a group of chemical compounds which contain silicon atom that can be covalently bonded to an alkoxy group. Thus, a silyl ether is formed.

The term "alkoxy" as used herein refers to a radical of the formula $-O-R^2$, where $R^2$ is a group having an alkyl group attached to the oxygen atom.

The terms "deuteration" or "deuterating" and the like as used herein refers to incorporating deuterium at one or more positions of Formula I in place of hydrogen at that position (s). In one embodiment, the deuterium enrichment is about 15% or more, i.e., at least about 1000 times greater than the natural abundance of deuterium. In another embodiment, the deuterium enrichment is about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, about 98% or more, or about 99% or more. In another embodiment, the deuterium enrichment is about 100%. The deuterium enrichment can be determined using conventional analytical methods known to one of ordinary skill in the art, including mass spectrometry and nuclear magnetic resonance spectroscopy.

When a position of Formulae I is designated specifically as "H" or "hydrogen," the position is understood to have hydrogen at its natural abundance isotopic composition.

When a position of Formulae I is designated specifically as "D" or "deuterium," the position is understood to have deuterium at an abundance that is at least about 1000 times greater than the natural abundance of deuterium, which is about 0.015%.

In one embodiment, a deuterated compound of Formula I has the following structure:

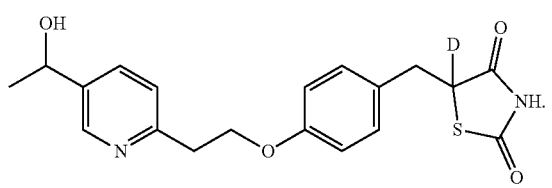 [SMILES: [2H]C1(Cc2ccc(OCCc3ccc(C(C)O)cn3)cc2)SC(=O)NC1=O]

See, the preparation in Example 8.

In another embodiment, deuterium is incorporated at more than one available position of Formula I, e.g., 1, 2, 3, 4, 5, or 6 available positions. In another embodiment, deuterium is incorporated at all available positions of Formula I. Deuterated starting compounds can used to prepare a deuterated compound of Formula I, or a pharmaceutically acceptable salt thereof. Such starting compounds can be, for example, deuterated acetaldehyde, deuterated ethylene oxide, or deuterated 4-hydroxybenzaldehyde.

In one embodiment, the disclosure provides a process for preparing the compound of Formula I illustrated by Scheme 2:

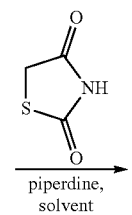

In another embodiment, the disclosure provides a process for preparing the compound of Formula I illustrated by Scheme 3:

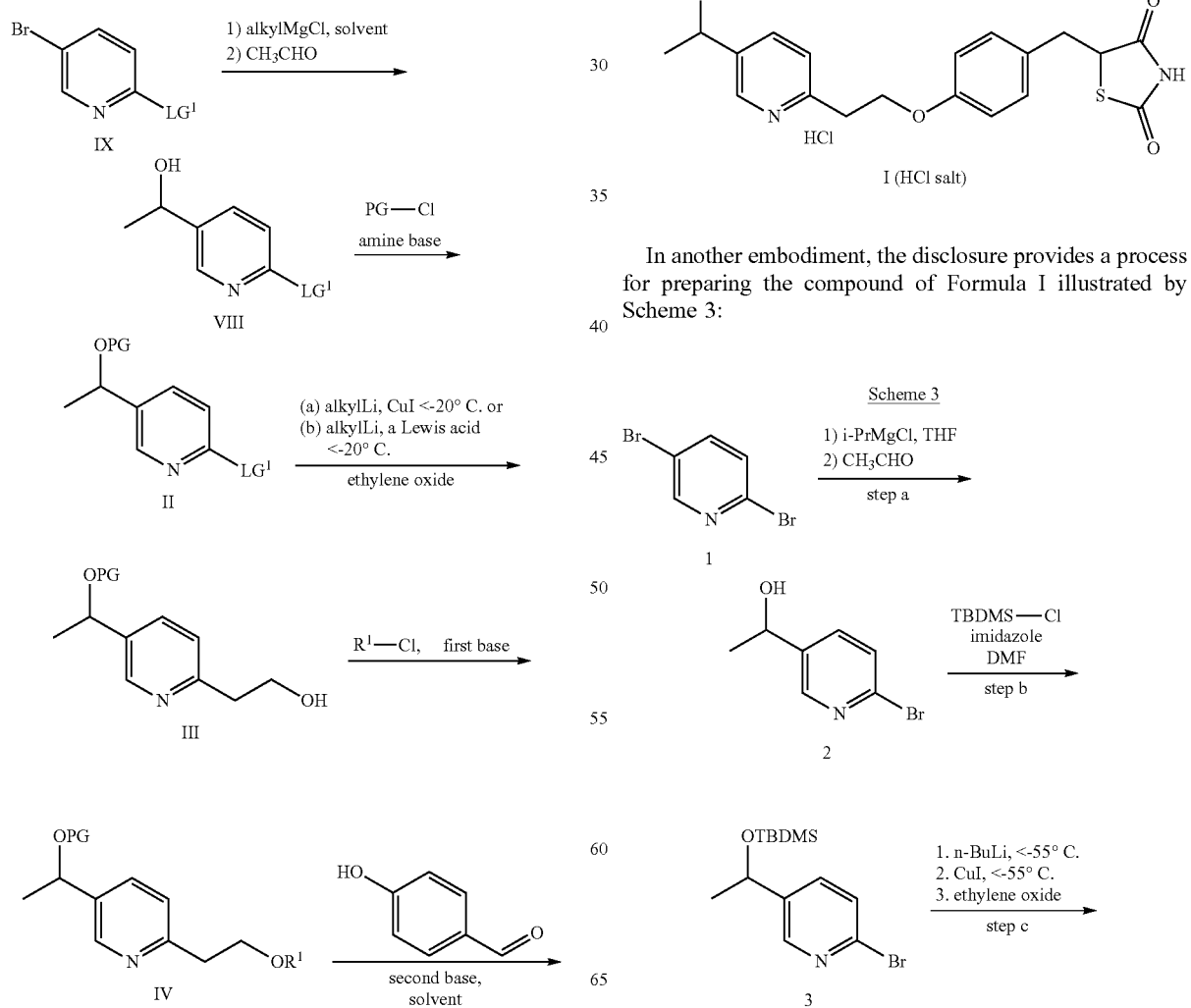

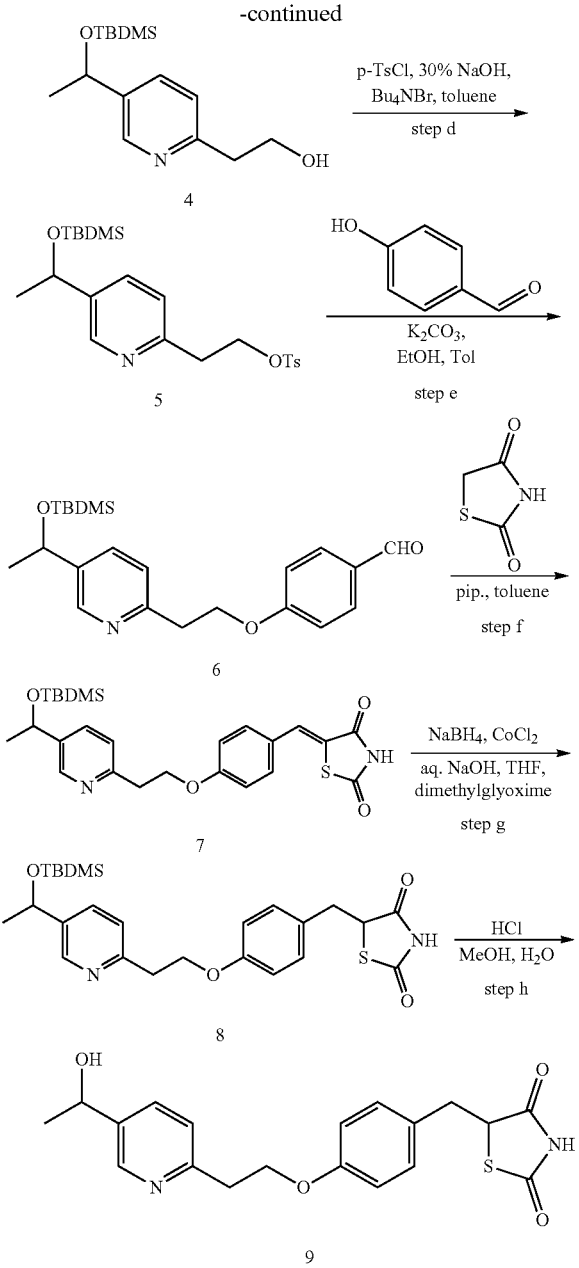

Cu(I)iodide while maintaining the reaction temperature, i.e., the reaction mixture temperature, below −20° C. In one embodiment, the reaction temperature is maintained below −55° C. while adding n-BuLi and Cu(I)iodide into the reaction mixture. In another embodiment, the temperature of the reaction mixture is maintained below −55° C. while adding n-BuLi, followed by ethylene oxide and then Cu(I) iodide into the reaction mixture. In another embodiment, the temperature of the reaction mixture is maintained below −55° C. while adding n-BuLi into the reaction mixture, followed by ethylene oxide. In this embodiment, Cu(I)iodide is added then into the reaction mixture while the reaction mixture temperature is maintained below −20° C., and preferably below −55° C. The reaction mixture is then allowed to slowly warm to room temperature after the addition of the reagents and stirred at room temperature, e.g., 20-25° C., overnight. This process is described in detail in Example 2. After the reaction, the complexed copper is advantageously removed by washing with 10% ammonia. The crude compound 4 can be purified by column chromatography to give >99% pure product with a yield of about 52%.

The following examples are illustrative, but not limiting, of the methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Comparative Example 1

Synthesis of 5-[[4-[2-[5-(1-hydroxyethyl)-2-pyridinyl]ethoxy]phenyl]methyl]-2,4-thiazolidinedione (9a) According to the Process Described in WO 2015/150476 A1

In another embodiment in Scheme 3, step c, the order of mixing of the reagents can be as follows: 1. n-BuLi, 2. ethylene oxide, and 3. CuI. This order of mixing is described in Example 2.

In the step a, 2,5-dibromopyridine (1) is reacted with i-PrMgCl in THF and then further with acetaldehyde to obtain compound 2. The reaction mixture is preferably filtered over Celite® after the reaction to remove most of the salts. In one embodiment, the addition of acetaldehyde is conducted at a temperature between −15° C. and −10° C. to control the exothermic reaction.

In the step b, compound 2 is reacted with TBDMS-Cl in the presence of imidazole having DMF as a solvent. The crude product 3 is advantageously purified by a short plug filtration.

In the step c, the hydroxyl protected compound 3 is reacted with ethylene oxide in the presence of n-BuLi and

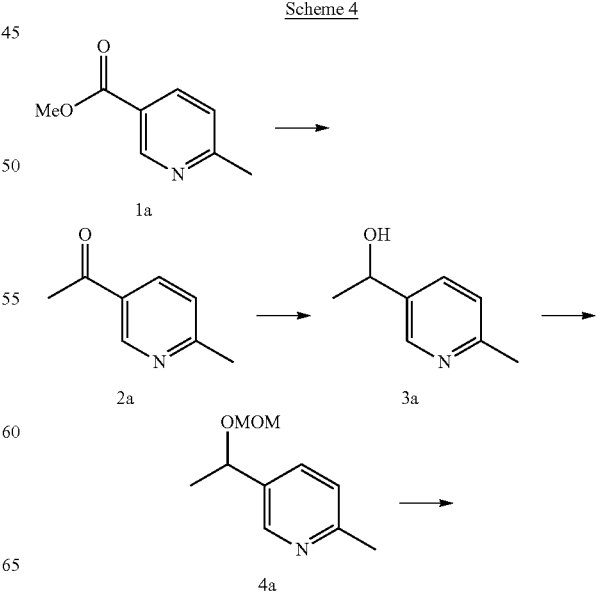

Scheme 4

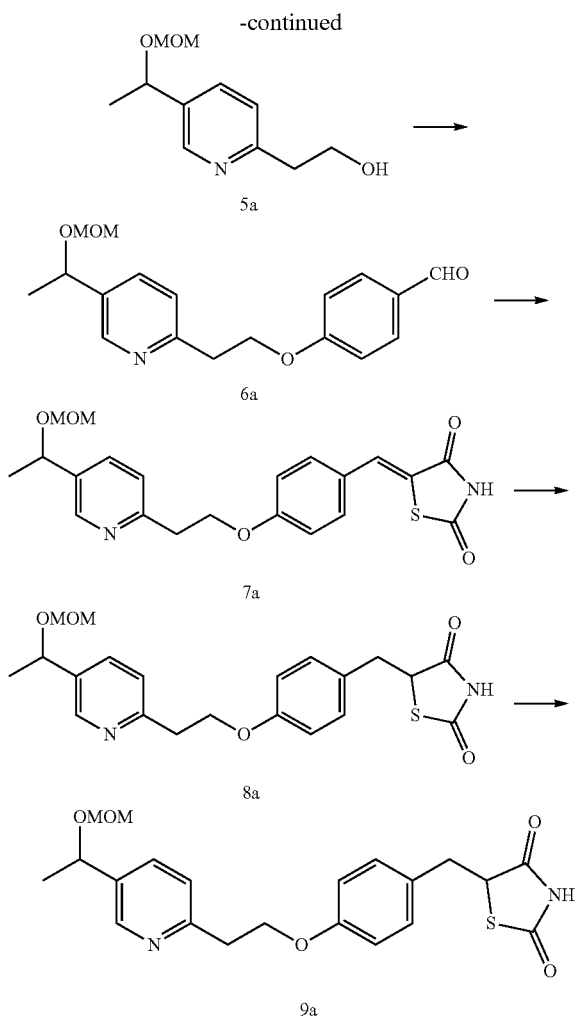

(a) Synthesis of 1-(6-methyl-pyridin-3-yl)-ethanol (3a)

LiHMDS (1.0 M in tetrahydrofuran, 463 ml, 0.463 mol) was added drop wise to a cooled solution of methyl 6-methylnicotinate (1a) (20 g, 0.132 mol) and ethyl acetate (82 g, 0.927 mol) in dimethylformamide at −50° C.; gradually raised the temperature to room temperature and stirred at the same temperature. After 1 h, the reaction mixture was cooled to 0° C.:slowly diluted with 20% sulphuric acid and heated to reflux. After 4 h, the reaction mixture was cooled to room temperature. and further to 0° C. and basified with potassium carbonate. The reaction medium was diluted with water and extracted in ethyl acetate (3×50 mL). Combined organic extract was dried over sodium sulphate and concentrated to afford crude 1-(6-methylpyridin-3-yl)ethan-1-one (2a) (20.0 g) which was taken to the next step without any purification. ES-MS [M+1]+: 136.1.

Sodium borohydride (2.3 g, 0.06 mol) was added in small portions over 30 min, to a solution of compound 2a (16.4 g, 0.121 mol) in ethanol (160 mL) at 0° C. and the reaction mixture was stirred at same temperature. After 1 h, the reaction mixture was diluted with sodium bicarbonate solution (sat) (2×200 mL) and extracted with dichloromethane (2×500 mL). The combined organic extract was dried over anhydrous sodium sulphate and concentrated to afford a pale yellow oil, which was purified by flash column chromatography (5% methanol/dichloromethane) to afford compound 3a (17.0 g; 93% yield over 2 steps) as a pale yellow oil. ES-MS [M+1]+: 138.1. $^1$H NMR (400 MHz, CDCl$_3$): δ 8.35 (d, J=2.0 Hz, 1H), 7.63 (dd, J=8.0, 2.4 Hz, 1H), 7.12 (d, J=8.0 Hz, 1H), 4.89 (q, J=6.5 Hz, 1H), 3.30 (br s, 1H), 2.50 (s, 3H), 1.48 (d, J=6.5 Hz, 3H).

(b) Synthesis of 5-(1-methoxymethoxy-ethyl)-2-methyl-pyridine (4a)

Compound 3a (15 g, 0.109 mol) was added, drop wise, to a cooled suspension of sodium hydride (6.56 g, 0.164 mol) in tetrahydrofurane (150 mL) and stirred at 0° C. After 30 min, chloromethyl methyl ether (13.2 g, 0.164 mol) was added drop wise while stirring and keeping the internal temperature around 0° C. After addition is over, the reaction mixture was stirred at the same temperature for 1 h. The reaction was quenched with ice cold water (80 mL) and extracted with ethyl acetate (3×50 mL). The combined organic extract was dried over anhydrous sodium sulphate and concentrated to afford an orange color oil, which was purified by flash column chromatography (1% methanol/dichloromethane) to afford compound 4a (10.0 g: 51% yield) as a pale yellow oil. ES-MS [M+1]+: 182.2. $^1$H NMR (400 MHz, CDCl$_3$): δ 8.45 (d, J=2.0 Hz, 1H), 7.56 (dd, J=8.0, 2.0 Hz, 1H), 7.14 (d, J=8.0 Hz, 1H), 4.75 (q, J=6.4 Hz, 1H), 4.57 (ABq, 2H), 3.36 (s, 3H), 2.53 (s, 3H), 1.48 (d, J=6.6 Hz, 3H).

(c) Synthesis of 2-[5-(1-methoxymethoxy-ethyl)-pyridin-2-yl]-ethanol (5a)

A mixture of compound 4a (7.0 g, 0.0386 mol) and 37% formaldehyde solution (5.8 g, 0.077 mol) was heated to 160° C. in a sealed glass tube for 5 h. The reaction mixture was cooled to room temperature and concentrated under reduced pressure to afford a crude compound which was purified by flash column chromatography (1% methanol/dichloromethane) to afford compound 5 (1.2 g; 17% yield) as pale yellow oil. ES-MS [M+1]+: 212.1. $^1$H NMR (400 MHz, CDCl$_3$): δ 8.42 (d, J=2.0 Hz, 1H), 7.65 (dd, J=8.0, 2.4 Hz, 1H), 7.25 (d, J=8.0 Hz, 1H), 4.72 (q, J=6.6 Hz, 1H), 4.65 (t, J=5.6 Hz, 1H), 4.52 (ABq, 2H), 3.73 (m, 2H), 3.24 (s, 3H), 2.86 (t, J=7.2 Hz, 2H), 1.49 (d, J=6.4 Hz, 3H).

The total yield for compound 5a from compound 1a was 8% molar.

(d) Synthesis of 4-{2-[5-(1-methoxymethoxy-ethyl)-pyridin-2-yl]-ethoxy}-benzaldehyde (6a)

Methanesulphonylchloride (1.19 g, 0.01 mol) was added, drop wise, to a cooled suspension of compound 5a (1.7 g, 0.008 mol) and triethylamine (1.79 ml, 0.013 mol) in dichloromethane (20 mL) at 0° C. and stirred at same temperature for 1 h. The reaction mixture was diluted with water (50 mL) and extracted with dichloromethane (3×50 mL). The combined organic extract was dried over anhydrous sodium sulphate and concentrated to afford 2-(5-(1-(methoxymethoxy)ethyl)pyridin-2-yl)ethyl methanesulfonate (2.04 g; 88% yield) as a yellow oil, which was taken to next step without purification. ES-MS [M+1]+: 290.

2-(5-(1-(methoxymethoxy)ethyl)pyridin-2-yl)ethyl methanesulfonate was added (2.3 g, 0.008 mol) to a stirred suspension of 4-hydroxybenzaldehyde (1.65 g, 0.0137 mol) and potassium carbonate (1.86 g, 0.0137 mol) in mixture of toluene (25 mL) and ethanol (25 mL); stirred at 85° C. for 5 h. After consumption of the starting materials, the reaction mixture was diluted with water (30 mL) and extracted with ethyl acetate (2×100 mL). The combined organic extract was washed with water; dried over anhydrous sodium sulphate and concentrated to afford a crude dark yellow liquid. The crude was purified by flash column chromatography (1% methanol/dichloromethane) to afford compound 6a (1.5 g; 60% yield) as pale yellow liquid. ES-MS [M+1]$^+$: 316.1.

(e) Synthesis of 5-(4-{2-[5-(1-methoxymethoxy-ethyl)-pyridin-2-yl]-ethoxy}-benzylidene)-thiazolidine-2,4-dione (7a)

Piperidine (80 mg, 0.95 mmol) was added to a solution of compound 6a (0.6 g, 1.9 mmol) and thiazolidine-2,4-dione (0.22 g, 1.9 mmol) in ethanol (15 mL) and the mixture was heated to reflux overnight. After 15 h, the reaction mixture was cooled to room temperature and concentrated under reduced pressure to afford crude mixture, which was purified by flash column chromatography (2% methanol/dichloromethane) to afford compound 7 (500 mg; 64% yield) as a yellow solid. ES-MS [M+1]+: 415.1. $^1$H NMR (400 MHz, DMSO-d$_6$): δ 12.25 (br s, 1H), 8.47 (d, J=2.0 Hz, 1H), 7.70 (dd, J=8.0, 2.0 Hz, 1H), 7.54 (d, J=8.8 Hz, 2H), 7.36 (d, J=8.0 Hz, 1H), 7.21 (d, J=8.8 Hz, 2H), 4.73 (m, 1H), 4.60-4.40 (m, 4H), 4.22 (t, J=6.2 Hz, 2H), 3.24 (s, 3H), 3.20 (t, J=6.8 Hz, 2H), 1.41 (d, J=6.0 Hz, 3H).

(f) Synthesis of 5-(4-{2-[5-(1-hydroxy-ethyl)-pyridin-2-yl]-ethoxy}-benzyl)-thiazolidine-2,4-dione (9a)

A solution of sodium borohydride (115 mg, 3.017 mmol) in 0.2N sodium hydroxide (1.2 mL) was added slowly to a stirred solution of compound 7 (0.5 g, 1.207 mmol), dimethylglyoxime (42 mg, 0.36 mmol) and CoCl$_2$.6H$_2$O (23 mg, 0.096 mmol) in a mixture of water (6 mL):tetrahydrofurane (6 mL) and 1M sodium hydroxide (1 mL) solution at 10° C. and after addition, the reaction mixture was stirred at room temperature. After 1 h, the reaction color lightened and additional quantities of sodium borohydride (46 mg, 1.207 mmol) and CoCl$_2$.6H$_2$O (22 mg, 0.096 mmol) were added and stirring was continued at room temperature. After 12 h, the reaction was neutralized with acetic acid (pH~7); diluted with water (10 mL) and extracted in ethyl acetate (3×50 mL). The combined organic extract was dried over anhydrous sodium sulphate and concentrated to afford crude compound 8a, 5-(4-(2-(5-(1-(methoxymethoxy)ethyl)pyridin-2-yl)ethoxy)benzyl)thiazolidine-2,4-dione, (0.4 g) as pale yellow semi solid, which was taken to next step without purification. ES-MS [M+1]$^+$: 417.5.

2N HCl (2 mL) was added to a solution of compound 8a (0.4 g, 0.96 mmol) in methanol (20 ml) and the mixture was heated to reflux. After 4 h, the reaction mixture was cooled to room temperature and then concentrated under reduced pressure to afford a residue which was dissolved in water and the solution was neutralized using sodium bicarbonate solution (sat). The resulting white precipitate was collected by filtration to afford compound 9a (250 mg; 56% yield over 2 steps) as an off-white solid. ES-MS [M+1]+: 373.4. $^1$H NMR (400 MHz, DMSO-d$_6$): δ 12.00 (br s, —NH), 8.46 (d, J=2.0 Hz, 1H), 7.66 (dd, J=8.0, 2.4 Hz, 1H), 7.30 (d, J=8.0 Hz, 1H), 7.13 (d, J=8.4 Hz, 2H), 6.86 (d, J=8.4 Hz, 2H), 5.25 (d, J=4.4 Hz, 1H), 4.86 (m, 1H), 4.75 (m, 1H), 4.30 (t, J=6.8 Hz, 2H), 3.30 (m, 1H), 3.14 (t, J=6.4 Hz, 2H), 3.04 (m, 1H), 1.34 (d, J=6.4 Hz, 3H).

The overall yield of compound 9a was 1.5% molar.

Example 2

Synthesis of 2-(5-(1-((tert-butyldimethylsilyl)oxy)ethyl)pyridin-2-yl)ethan-1-ol The synthesis of 2-(5-(1-((tert-butyldimethylsilyl)oxy)ethyl)pyridin-2-yl)ethan-1-ol was conducted according to the Scheme 5 using the reagents and solvents listed in Table 1 below:

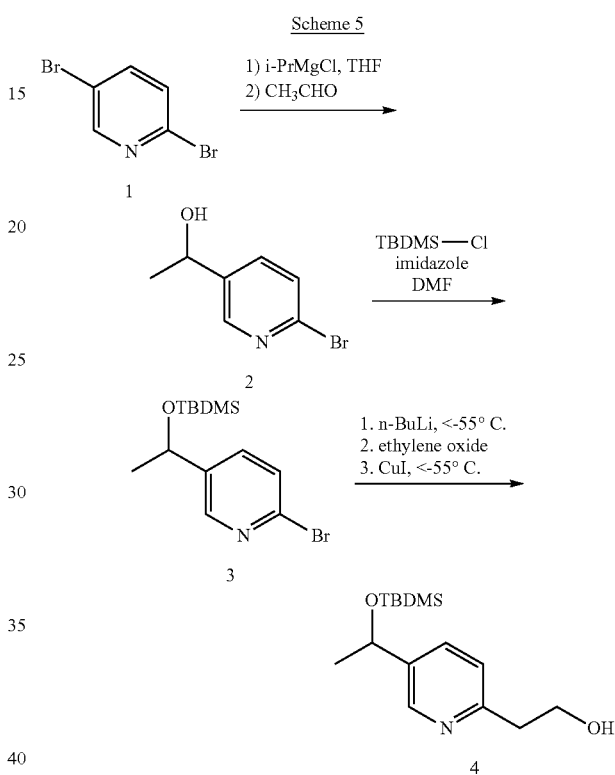

Scheme 5

The 1H-NMR spectra were recorded with Agilent MercuryPlus 300 NMR spectrometer.

LC-MS data were obtained on an Agilent 1290 series with UV detector and HP 6130 MSD mass detector using as column Waters XBridge BEH XP (2.1×50 mm; 2.5 µm) and as eluent Ammonium acetate (10 mM); Water/Methanol/Acetonitrile.

(a) 1-(6-bromopyridin-3-yl)ethan-1-ol (2)

A 20 L vessel was placed under nitrogen atmosphere and charged with tetrahydrofuran (5.5 L) and 2,5-dibromopyridine (1) (2000 g, 8.44 mol, 1.0 eq) (OxChem Corporation). The mixture was cooled to −10° C. and isopropyl magnesium chloride (20% in THF, 6.02 L, 11.82 mol, 1.4 eq) (Rockwood Lithium) was added slowly over 1 h, keeping the reaction temperature below 5° C. After addition, the cooling bath was removed and the temperature was kept below 30° C. (some additional cooling was needed to achieve this) and the reaction mixture was stirred overnight. After 16 h, a sample was taken; quenched with saturated aqueous ammonium chloride and extracted with methyl tert-butyl ether (TBME). The TBME was evaporated under vacuum. $^1$H-NMR in deuterated chloroform showed complete conversion.

The reaction mixture was cooled to −15° C. and a solution of acetaldehyde (472 g, 10.72 mol, 1.27 eq) (Acros) in tetrahydrofuran (200 mL) was added dropwise, while keeping temperature below −10° C. After the addition was complete, the cooling bath was removed and the temperature was allowed to rise to maximum of 5-8° C. After 1.5 h, a sample was taken and the reaction was quenched with aqueous ammonium chloride as described above, $^1$H-NMR showed the reaction was complete.

Two batches were combined for work up.

The reaction mixture was quenched by pouring the mixture into a solution of aqueous ammonium chloride (1 kg in 5 L water) and stirred for 15 min, filtered over Celite® and rinsed thoroughly with toluene. The filtrate was transferred to a separation funnel and the obtained two layers system was separated. The aqueous layer was extracted with toluene (2 L). The combined organic layers were dried over sodium sulfate and filtered. Evaporation of the filtrate to dryness under vacuum yielded 3.49 kg (99%) of the desired crude material. $^1$H NMR (300 MHz, CDCl$_3$): δ 8.30 (d, J=2.5 Hz, 1H), 7.59 (dd, J=8.0, 2.5 Hz, 1H), 7.44 (d, J=8.0 Hz, 1H), 4.91 (q, J=6.5 Hz, 1H), 1.49 (d, J=6.5 Hz, 3H).

(b) 2-bromo-5-(1-((tert-butyldimethylsilyl)oxy) ethyl)pyridine (3)

A 50 L reactor under nitrogen atmosphere was charged with compound 2 (10.0 kg, around 49.5 mol) and DMF (16 L). The mixture was cooled to 10° C. and imidazole (6.74 kg, 99 mol, 2.0 eq) (Apollo Scientific Ltd.) was added portion wise within 30 min. The mixture was cooled to 0° C. and TBDMS-Cl (7.46 kg, 49.5 mol, 1.0 eq) (Fluorochem) was added portion wise within 5 h, keeping the temperature below 3° C. The mixture reaction temperature was allowed to reach room temperature and stirred overnight. $^1$H NMR of a sample showed complete conversion.

The reaction mixture was transferred to a 100 L extraction-vessel and the product was extracted with heptane (2×7.5 L, 10 L). The combined heptane-layers were washed with water (2×6 L, 3 L) to remove small amounts of DMF, dried over sodium sulfate and evaporated under vacuum to give crude compound 3 (15.5 kg, 49.0 mol) in a 99.0% yield. This crude product was purified by a short plug filtration, using 10 kg silica/heptane and eluted with heptane (approx. 50 L). The product-fractions were combined and evaporated under vacuum to give 12.0 kg of purified compound 3 (38 mol) as a brown oil in a 76.8% molar yield. (Average yield for 3 experiments was 78%). HPLC-MS: Rt=2.6 min, M+1=316.1 and 318.1; $^1$H NMR (300 MHz, CDCl$_3$): δ 8.55 (d, J=2.2 Hz, 1H), 7.54 (dd, J=8.2, 2.2 Hz, 1H), 7.42 (d, J=8.2 Hz, 1H), 4.86 (q, J=6.5 Hz, 1H), 1.40 (d, J=6.5 Hz, 3H), 0.88 (s, 9H), 0.02 (d, J=26 Hz, 2×3H).

(c) 2-(5-(1-((tert-butyldimethylsilyl)oxy)ethyl)pyridin-2-yl)ethan-1-ol (4)

The ethylene oxide solution in diethylether was prepared in advance. Diethylether (1.2 L) in a 3 L three-necked flask was cooled at −65° C. and ethylene oxide (462.3 g, 10.5 mol, 1.06 eq) (Linde) was added and stirred at −70° C. Alternatively, the ethylene oxide solution can be made at about −20° C. and then added gradually to the reaction mixture having a temperature at about −60° C.

To a solution of 2-bromo-5-(1-((tert-butyldimethylsilyl) oxy)ethyl)pyridine (3) (3.13 kg, 9.90 mol, 1.0 eq) in diethyl-ether (7.5 L) cooled at −59° C., n-butyllithium (4 L, 10.0 mol, 2.5M in hexanes, 1.01 eq) (Aldrich Chemistry) was added while keeping temperature between −58° C. and −62° C. After addition, the mixture was stirred for 1 h while keeping temperature between −60° C. and −68° C. The upfront prepared ethylene oxide solution was added at once to the reaction mixture, while temperature was around −62° C. Subsequently, copper(I) iodide (962.3 g, 5.05 mol, 0.51 eq) (Acros Organics) was added in portions of 120 g, every 10 min, keeping the temperature between −61° C. and −63° C. Stirring was continued for 1 h after addition keeping temperature between −61° C. and −63° C. The cooling bath was removed and allowing the temperature to rise to about 15° C. and further to 25° C. with a water bath overnight.

Workup: The reaction-mixture was poured into a solution of 1 kg ammonium-chloride in 5 L water and stirred for 30 min, then the layers were separated. The organic layer was washed with aqueous ammonium hydroxide (10%, 2.5 L, 4×) to remove Cu-complex (blue color disappeared). The combined organic layers were dried over sodium sulfate and evaporated to give 3.12 kg (max. 9.90 mol) crude compound 4 as a brown oil. The crude compound was purified over 20 kg silica (heptane/EtOAc) by eluting with 80 L heptane/ EtOAc, 20 L EtOAc, 25 L EtOAc/MeOH 95/5, 25 L EtOAc/MeOH 9/1 and 10 L EtOAc/MeOH 8/2, to give 1.47 kg of purified compound 4 (5.22 mol) as a brown oil (with tendency to solidify) in a 52.7% average molar yield (HPLC-purity of 99.5%). (Average yield over 12 experiments 52%). HPLC-MS: Rt=2.3 min, M+1=282.1; $^1$H NMR (300 MHz, CDCl$_3$): δ 8.42 (d, J=2.1 Hz, 1H), 7.61 (dd, J=8.3, 2.1 Hz, 1H), 7.11 (d, J=8.3 Hz, 1H), 4.88 (q, J=7.0 Hz, 1H), 4.01 (t, J=6.0 Hz, 2H), 3.00 (t, J=6.0 Hz, 2H), 1.41 (d, J=7.0 Hz, 3H), 0.90 (s, 9H), 0.02 (d, J=26 Hz, 2×3H).

Another 2.5% of the product was isolated by re-purifying impure product fraction. The total yield of compound 4 from compound 1 was 39.6% molar.

Example 3

Synthesis of 5-[[4-[2-[5-(1-hydroxyethyl)-2-pyridinyl]ethoxy]phenyl]methyl]-2,4-thiazolidinedione hydrochloride (9)

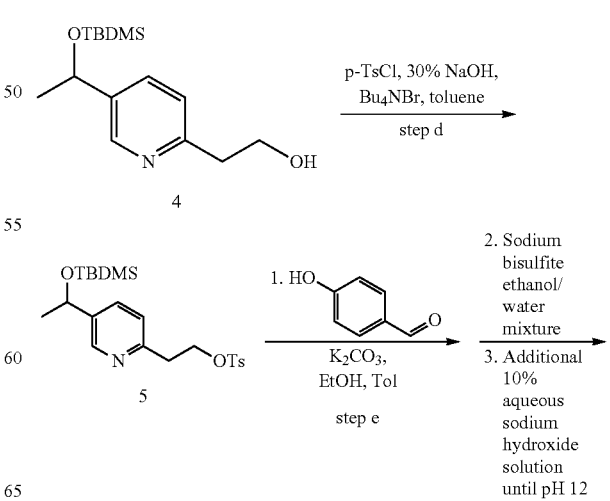

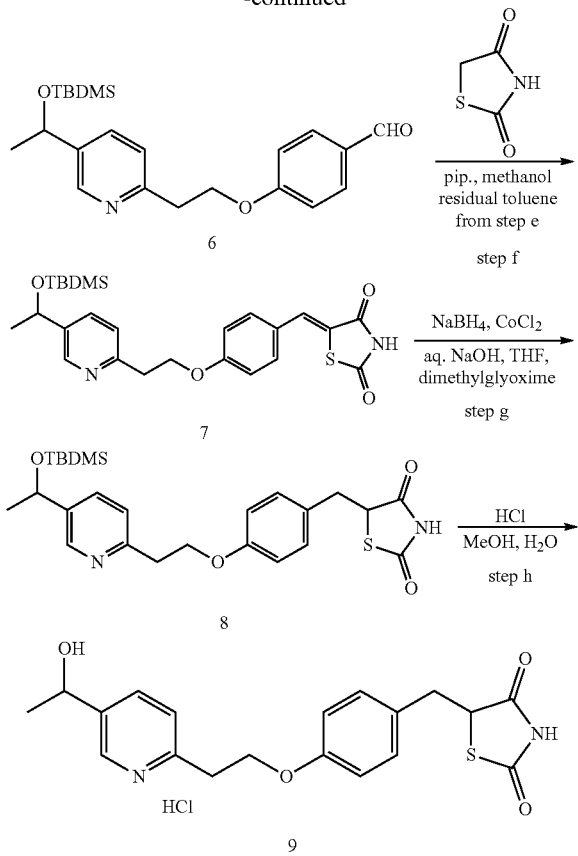

The ¹H-NMR spectra were recorded with a 400 MHz Avance Bruker NMR spectrometer. LC-MS data were obtained on a Agilent Technologies 6130 Quadrapole LC/MS using as column Agilent XDB-C18 and as eluent 0.1% formic acid (aq) and 0.05% formic acid in acetonitrile.

Steps d and e: Synthesis of 4-[2-[5-[[[(1,1-dimethylethyl)dimethylsilyl]oxy]ethyl]-2-pyridinyl]ethoxy]-benzaldehyde (6)

To a well stirred solution of 5-[[[(1,1-dimethylethyl)dimethylsilyl]-oxy]ethyl]-2-pyridineethanol (4) (obtained as described in Example 2) (1.91 kg) in toluene (8.6 L) at 5° C. were added sodium hydroxide (30% aqueous, 2.79 L) and tetrabutylammonium bromide (7.2 g). p-Toluenesulfonyl chloride (1.62 kg) was next added in portions during 5 min. After the addition, the reaction mixture was allowed to reach room temperature in 0.5 h and stirred at this temperature for 18 h. Water (7.3 L) was then added and the mixture was mixed well. Once the solids were dissolved, the layers were allowed to settle and the organic layer was separated. This organic phase was washed with water (5.7 L, 2×), followed by washing with a solution of sodium chloride (57 g) in water (5.7 L). The solvents were concentrated at reduced pressure to an amount of 2.5 kg of a brown oil (compound 5).

To this well stirred brown oil were added subsequently ethanol (7.8 L), water (0.86 L), 4-hydroxybenzaldehyde (0.88 kg) and potassium carbonate (1.17 kg) and then the mixture was heated at 75° C. for 18 h. Then, the solvent was evaporated while adding toluene (7.7 L) during 6 h and then the reaction mixture was allowed to cool. At 30° C., water (7.6 L) was added, stirred until all solids were dissolved and the mixture was cooled to room temperature. The layers were allowed to settle and separated. The organic layer was washed with water (7.6 L). The first aqueous extract was extracted with toluene (2.8 L) and this organic extract was used to also extract the aqueous washing. The organic extracts were combined and concentrated under vacuum to give 3.49 kg of a black oil (crude title compound 6).

1.73 kg of this black oil was dissolved in ethanol (0.74 L) and added to a well stirred solution of sodium bisulfite (1.36 kg) in a mixture of water (3.27 L) and ethanol (0.74 L). The container of the black oil was rinsed with ethanol (0.37 L) twice and these two rinses were also added to the bisulfite reaction mixture. After 75 min, heptane (5.3 L) was added, well mixed for 5 min, and the layers were allowed to settle and separated. To the organic layer was added a solution of sodium bisulfite (0.55 kg) in water (2.65 L), and ethanol (1.06 L). After stirring for 30 min, the layers were allowed to settle and separated. The two bisulfide aqueous extracts were combined and flasks rinsed with water (2.12 L). Next, toluene (4.5 L) and heptane (4.5 L) were added, the mixture was well stirred and the pH was adjusted to 12 using sodium hydroxide (10% aq) (temperature became 32° C.). After stirring for an additional 5 min, the layers were allowed to settle and separated at 30° C. The aqueous layer was extracted with a mixture of toluene (1.5 L) and heptane (3.0 L). The layers were separated and the organic layers were combined. The combined organic layers were washed with water (5 L, 2×) and concentrated under vacuum to give the purified title compound 6. This procedure was repeated with another 1.73 kg of the black oil (crude title compound 6) to give in total 2.77 kg of 4-[2-[5-[[[(1,1-dimethylethyl)dimethylsilyl]oxy]ethyl]-2-pyridinyl]ethoxy]-benzaldehyde (6) as brown oil which contained 24% m/m of toluene according to ¹H NMR (yield=80%, calculated from compound 4 and corrected for residual toluene).

¹H NMR (CDCl₃) δ: 0.00 (s, 3H), 0.09 (s, 3H), 0.91 (s, 9H), 1.44 (d, J=6 Hz, 3H), 3.30 (t, J=7 Hz, 2H), 4.47 (t, J=7 Hz, 2H), 4.92 (q, J=6 Hz, 1H), 6.99-7.30 (m, 3H), 7.62-7.67 (m, 1H), 7.80-7.85 (m, 2H), 8.5-8.54 (m, 1H) and 9.88 (s, 1H).

LC-MS; rt 7.5 min: ES: M⁺ 387, 386.

Step f: Synthesis of (5Z)-5-[[4-[2-[5-[[[(1,1-dimethylethyl)dimethylsilyl]oxy]ethyl]-2-pyridinyl]ethoxy]phenyl]methylene]-2,4-thiazolidinedione (7)

A solution of 4-[2-[5-[[[(1,1-dimethylethyl)dimethylsilyl]oxy]ethyl]-2-pyridinyl]-ethoxy]-benzaldehyde (6) (2.75 kg, containing 24% m/m of toluene) and piperidine (6.0 g) in methanol (3.16 L) was concentrated at 40° C. under reduced pressure. The residue was dissolved in methanol (10.4 L) and 2,4-thiazolidinedione (759 g) and piperidine (230 g) were added. The mixture was heated at 47° C. After 25 h, the reaction mixture was allowed to cool to room temperature. The mixture was kept at pH 5-6 by adjusting it with acetic acid, if necessary. After a night at room temperature, water (1.56 L) was added and the suspension was stirred at room temperature for additional 2 h. The solids were isolated by filtration, washed with methanol (1 L, 2×) and dried under vacuum to give crude compound 7 (1.65 kg). The crude compound was mixed with methanol (10 L) and dichloromethane (8.6 L) and heated at 32° C. until all solids dissolved. Then, the solvents were removed by distillation until the temperature of the mixture reached 34° C. at a pressure of 333 mbar. Then, it was allowed to cool to room temperature overnight and stirred at 2° C. for additional 2 h.

The solids were isolated by filtration, washed with methanol (0.5 L, 2×) and dried under vacuum to give title compound 7 (1.50 kg) (yield=61%).

$^1$H NMR (CDCl$_3$) δ 0.00 (s, 3H), 0.08 (s, 3H), 0.90 (s, 9H), 1.43 (d, J=6 Hz, 3H), 3.32 (t, J=7 Hz, 2H), 4.48 (t, J=7 Hz, 2H), 4.92 (q, J=6 Hz, 1H), 6.95-7.00 (m, 2H), 7.24-7.28 (m, 1H), 7.38-7.42 (m, 2H), 7.67 (s, 1H), 7.69-7.73 (m, 1H) and 8.48 (d, J=3 Hz, 1H).

LC-MS: rt 7.5 min: ES: M$^+$ 487, 486, 485.

Step g: Synthesis of 5-[[4-[2-[5-[[[(1,1-dimethylethyl)dimethylsilyl]oxy]ethyl]-2-pyridinyl]ethoxy]phenyl]methyl]-2,4-thiazolidinedione (8)

To a stirred suspension of (5Z)-5-[[4-[2-[5-[[[(1,1-dimethylethyl)dimethylsilyl]oxy]-ethyl]-2-pyridinyl]ethoxy]phenyl]methylene]-2,4-thiazolidinedione (7) (10 g) in THF (10 mL) and sodium hydroxide (1N aq, 21 mL) was added of a solution of cobalt chloride (26 mg) and of dimethylglyoxime (930 mg) in THF (2.3 mL) and water (1.0 mL). Then the suspension was put under a nitrogen atmosphere by applying the sequence of vacuum and flushing with nitrogen (4×). Thereafter, the suspension was heated to 30° C. Then, a stock solution of sodium borohydride was prepared by dissolving sodium borohydride (2.7 g) in a mixture of water (15.8 mL) and a solution of sodium hydroxide (1 N aq, 3.5 mL), which was put under a nitrogen atmosphere by applying a sequence of vacuum and flushing with nitrogen (3×). This was added to the suspension of compound 7 at a rate of 4.5 mL/h. Simultaneously, nitrogen gas-saturated acetic acid was added to the suspension at a rate of 0.7 mL/h to maintain a pH of 10.0-10.5. After 1 h 30 min the rate of addition of the sodium borohydride solution and acetic acid were both reduced by half. Next, 3 h 45 min after start of addition, the addition of sodium borohydride and acetic acid were stopped. The mixture was allowed to cool down to room temperature and acetone (2.5 mL) was added over a period of 1 minute. After stirring the reaction mixture for 15 min acetic acid was added until the pH was 5.5-6.0 (about 3 mL required). Next, a mixture of ethyl acetate/toluene (1/3 v/v, 30 mL) was added, well mixed and layers were allowed to settle. The aqueous layer was separated and washed with ethyl acetate/toluene (1/3 v/v, 10 mL). Both organic extracts were pooled and water (40 mL) was added, well mixed and layers were allowed to settle. The pH of the aqueous layer was adjusted to 5.5-6 using saturated sodium hydrogen carbonate solution (aq) and again mixed with the organic layer. Layers were allowed to settle and the organic layer was separated and concentrated under vacuum to give 11.09 g of yellow oil (crude mixture containing title compound 8 and its borane complex). Several batches were combined for work up.

33.1 g of the crude mixture containing title compound 8 and its borane complex (not corrected for residual solvents) was dissolved in toluene (30 mL) and filtered. The filtrate was submitted to column chromatography (silica gel, gradient of toluene to toluene/ethyl acetate 1/1) to give 30.0 g of mixture of 5-[[4-[2-[5-[[[(1,1-dimethylethyl)dimethylsilyl]oxy]ethyl]-2-pyridinyl]ethoxy]phenyl]methyl]-2,4-thiazolidinedione (8) and its borane complex as a slightly yellow oil (yield=100% from compound 4, not corrected for residual solvents).

$^1$H NMR (CDCl$_3$) δ: –0.03-0.10 (m, 6H), 0.87-0.93 (m, 9H), 1.42 (d, J=6 Hz, 3H), 3.05-3.71 (m, 4H), 4.30-4.51 (m, 3H), 4.87-4.94 (m, 1H), 6.82-6.88 (m, 2H), 7.10-7.92 (m, 5H), 8.49 (d, J=3 Hz, 0.6H) and 8.72 (brs, 0.4H).

LC-MS; rt 6.8 min: ES: M$^+$ 489, 488, 487, M$^-$ 487, 486, 485; rt 8.1 min: ES M$^-$ 501, 500, 499, 498, 485.

Step h: Synthesis of 5-[[4-[2-[5-(1-hydroxyethyl)-2-pyridinyl]ethoxy]phenyl]-methyl]-2,4-thiazolidinedione hydrochloride (9)

To a stirred solution of the mixture of (5-[[4-[2-[5-[[[(1,1-dimethylethyl)-dimethylsilyl]oxy]ethyl]-2-pyridinyl]ethoxy]phenyl]methyl]-2,4-thiazolidinedione and its borane complex (8) (5.17 g) in methanol (25.2 mL) at 22° C. was added hydrochloric acid (30%, 2.75 mL) in about 5 min to give a temperature rise to 28° C. This solution was heated to 40° C. Three hours after addition, the 11 g of volatiles were removed under reduced pressure. Then, acetonitrile (40.3 mL) was added and the mixture was heated at reflux for 0.5 h. Next, the suspension was allowed to cool down to room temperature and stirred for 1 h at room temperature. Solids were isolated by filtration, washed with a mixture of acetonitrile/water (20/1 v/v, 10 mL) and with acetonitrile (10 mL) and dried under vacuum at 40° C. to give 4.00 g of white solids (crude 9) (yield=77%, not corrected for residual solvents).

Purification of 5-[[4-[2-[5-(1-hydroxyethyl)-2-pyridinyl]ethoxy]phenyl]methyl]-2,4-thiazolidinedione hydrochloride (9)

The crude mixture of 5-[[4-[2-[5-(1-hydroxyethyl)-2-pyridinyl]ethoxy]phenyl]-methyl]-2,4-thiazolidinedione hydrochloride (3.95 g, crude 9) was dissolved in methanol/water (7/2 v/v, 80 mL) by heating it to 49° C. To this solution was added washed norit (obtained by heating a suspension of norit (6 g) in methanol/water (7/2 v/v, 90 mL) at 45° C. for 1 h, then isolating the norit by filtration and washing it twice with methanol/water (7/2 v/v, 30 mL) and drying it under vacuum at 40° C.). Equipment was rinsed with methanol/water (7/2 v/v, 18 mL). After 0.5 h of stirring at 46° C., the warm suspension was filtered to remove the norit and filter was washed twice with methanol/water (7/2 v/v, 18 mL). The filtrate was concentrated under vacuum at a bath temperature of 60° C. to a mass of 11.8 g (1 v of compound and 2 v of water). To the suspension was added butanone (19.7 mL, 5 v) and the mixture was heated at a bath temperature of 95° C. Under distillation at a constant volume, butanone (95 mL) was added. Next, heating was stopped and the suspension was allowed to reach room temperature in about 0.5 h. Subsequently it was stirred for 0.75 h at room temperature. The solids were isolated by filtration, washed with a mixture of butanone/water (95/5 v/v, 18 mL) and butanone (18 mL) and dried under vacuum at 40° C. to give 3.57 g of compound 9 as white solids (yield=91%).

$^1$H NMR (DMSO-d$_6$): δ 12.00 (br s, —NH), 8.71 (d, J=2.0 Hz, 1H), 8.45 (dd, J=8.3, 1.7 Hz, 1H), 7.98 (d, J=8.3 Hz, 1H), 7.15 (d, J=8.7 Hz, 2H), 6.88 (d, J=8.7 Hz, 2H), 5.57 (s, OH), 4.95 (q, J=6.5 Hz, 1H), 4.86 (dd, J=8.9, 4.4 Hz, 1H), 4.40 (t, J=6.3 Hz, 2H), 3.49 (t, J=6.2 Hz, 2H), 3.29 (dd, J=14.2, 4.4 Hz, 1H), 3.06 (dd, J=14.2, 9.0 Hz, 1H), 1.41 (d, J=6.5 Hz, 3H).

LC-MS; rt 3.5 min: ES: M$^+$ 374, 373, M$^-$ 372, 371.

Example 4

Conditions Tested in the Preparation of Compound 5 in the Step d

The conditions described in Table 2 below were tested in the step d in the preparation of compound 5 from compound 4 providing a good yield of compound 5:

TABLE 2

| Entry | Reaction Conditions | Amount of p-Ts-Cl/Eq |
|---|---|---|
| 1 | Toluene/water/Bu$_4$NBr/NaOH | 1.05 |
| 2 | | 1.08 |
| 3 | | 1.07 |
| 4 | | 1.07 + 0.03 |
| 5 | | 1.07 |
| 6 | Et$_3$N/DCM | 1.18 |
| 7 | | 1.40 |
| 8 | Pyridine/DCM | 1.40 |

Example 5

Conditions Tested in the Preparation of Compound 6 in the Step e

The conditions described in Table 3 below were tested in the step e in the preparation of compound 6 from compound 5 providing a good yield of compound 6:

TABLE 3

| Entry | Solvent | Base | Temp. (° C.) | Run time (h) |
|---|---|---|---|---|
| 1 | Toluene/ethanol 6:4 | K$_2$CO$_3$ | 78 | 17 |
| 2 | Toluene | | | |
| 3 | Ethanol | | | |
| 4 | 2-propanol | | | |
| 5 | Toluene/2-propanol/water 3:2:1.8 | | | |
| 6 | 2-MeTHF | | | |
| 7 | Toluene/ethanol 6:4 | | 50 | |
| 8 | THF | | | |
| 9 | 2-MeTHF | Et$_3$N | 60 | |
| 10 | THF | KOtBu | | |

Example 6

Conditions Tested in the Preparation of Compound 7 in the Step f

The conditions described in Table 4 below were tested in the step f in the preparation of compound 7 from compound 6 providing a good yield of compound 7:

TABLE 4

| Entry | Condition | Temp. (° C.) |
|---|---|---|
| 1 | Toluene/piperidine | 74 |
| 2 | Ethanol/piperidine | 74 |
| 3 | Toluene/acetic acid/piperidine | 74 |
| 4 | Methanol/piperidine | 50 |

Example 7

Large Scale Synthesis of 5-[[4-[2-[5-(1-hydroxyethyl)-2-pyridinyl]ethoxy]phenyl]methyl]-2,4-thiazolidinedione hydrochloride (9)

Steps d, e, f, g, and h refer to the steps described in the scheme of Example 3 above. The $^1$H-NMR spectra and the LC-MS data of the compounds prepared were confirmed as described in Example 3.

Steps d and e: Synthesis of 4-[2-[5-[[[(1,1-dimethylethyl)dimethylsilyl]oxy]ethyl]-2-pyridinyl]ethoxy]-benzaldehyde (6)

To a well stirred solution of 5-[[[(1,1-dimethylethyl)dimethylsilyl]-oxy]ethyl]-2-pyridineethanol (4) (obtained as described in Example 2) (8.14 kg) in toluene (33 L) at 5° C. were added sodium hydroxide (30% aqueous, 11.65 L) and tetrabutylammonium bromide (30.13 g). p-Toluenesulfonyl chloride (6.76 kg) was next added, addition equipment rinsed with toluene (2 L) and rinse added to the reactor. After the addition, the reaction mixture was allowed to reach room temperature and stirred at this temperature overnight. Water (32 L) was then added and the mixture was mixed well. Once the solids were dissolved, the layers were allowed to settle and the organic layer was separated. This organic phase was washed with water twice (24 L, 2×). The solvents were evaporated partly at reduced pressure to yield a residue of 29.5 kg of a brown oil (compound 5).

To this well stirred brown oil were added ethanol (32 L), water (3.6 L), 4-hydroxybenzaldehyde (3.69 kg) and potassium carbonate (4.87 kg) and then the mixture was heated at 75° C. overnight. Next, toluene (32 L) was added and volatiles (32 L) were evaporated. Subsequent, the reaction mixture was allowed to cool. At 20° C., water (32 L) was added, stirred until all solids were dissolved and the mixture was cooled to room temperature. The layers were allowed to settle and separated. The organic layer was washed with water (32 L). The first aqueous extract was extracted with toluene (12 L) and this organic extract was used to also extract the aqueous washing. The organic extracts were combined and concentrated under vacuum to give 15.6 kg of a black oil (crude title compound 6 containing residual toluene). This procedure was repeated using 8.14 kg of compound 4 to give another 13.3 kg of a black oil (crude title compound 6 containing residual toluene).

Both batches of crude compound 6 were pooled. 4.76 kg of this pooled black oil was concentrated in vacuo, dissolved in ethanol (0.9 L) and added to a well stirred solution of sodium bisulfite (7.3 L of a stock solution prepared by dissolving 2.91 kg of sodium bisulfite in 10 L of water) and ethanol (1.1 L). The container of the black oil was rinsed with ethanol (0.55 L 2×) twice and these two rinses were also added to the bisulfite reaction mixture. After 75 min, heptane (8 L) was added, well mixed for 15 min, the layers were allowed to settle and separated. To the organic layer was added a solution of sodium bisulfite (2.8 L of a stock solution prepared by dissolving 2.91 kg of sodium bisulfite in 10 L of water), water (2.4 L) and ethanol (1.6 L). After stirring for 30 min, the layers were allowed to settle and separated. The two bisulfide aqueous extracts were combined and flasks rinsed with water (3.2 L). Next, toluene (7 L) and heptane (7 L) were added, the mixture was well stirred and the pH was adjusted to 12 using sodium hydroxide (10% aq) (temperature became 28° C.). After stirring for additional 20 min, the layers were allowed to settle and separated at 30° C. The aqueous layer was extracted with a mixture of toluene (2.3 L) and heptane (4.6 L). The layers were separated and the organic layers were combined. The combined organic layers were washed with water (7.7 L) and concentrated under vacuum to give the purified title compound 6 (4.17 kg containing 1.06 kg of toluene and 3.11 kg of compound 6). This procedure was repeated with the remaining 24 kg of the black oil (crude title compound 6) and in two runs gave in total an additional 14.23 kg of 4-[2-[5-[[[(1,1-dimethylethyl)dimethylsilyl]oxy]ethyl]-2-pyridinyl]ethoxy]-benzaldehyde (6) as brown oil corrected for residual of toluene (based on $^1$H NMR) and 0.13 kg of compound 6 as equipment rinse in methanol (total yield=79%, calculated from compound 4 and corrected for solvents).

Step f: Synthesis of (5Z)-5-[[4-[2-[5-[[[(1,1-dimethylethyl)dimethylsilyl]oxy]ethyl]-2-pyridinyl]ethoxy]phenyl]methylene]-2,4-thiazolidinedione (7)

A solution of 4-[2-[5-[[[(1,1-dimethylethyl)dimethylsilyl]oxy]ethyl]-2-pyridinyl]-ethoxy]-benzaldehyde (6) (14.36 kg of compound 6 in toluene/methanol), toluene (22.2 L), piperidine (44 g) and methanol (14.5 L) was concentrated at 45° C. (jacket temperature) under reduced pressure. The residue was dissolved in methanol (61.6 L) and 2,4-thiazolidinedione (5257 g) and piperidine (1544 g) were added. The addition equipment was rinsed with methanol (in total 10.8 L), rinse also added to the reaction mixture and the mixture was heated at 47° C. After 28 h, the reaction mixture was allowed to cool to room temperature. The pH mixture was adjusted to pH 5-6 by addition of acetic acid (0.73 kg was required). After a night at room temperature, water (10.9 L) was added and the suspension was stirred at room temperature for additional 2 h. The solids were isolated by filtration, washed with methanol (7.3 L) and dried under vacuum to give crude compound 7 (13.6 kg). The crude compound was mixed with methanol (16 L) and dichloromethane (54 L) and heated at 32° C. until all solids dissolved. Then, solvent was removed by distillation under reduced pressure at jacket temperature of 45° C. keeping a constant volume by addition of methanol until the temperature of the mixture reached 34° C. at a pressure of 333 mbar (84 L of distillate was removed and 84 L of methanol were added). Then, it was stirred at a setpoint jacket temperature of 2° C. for one hour. The solids were isolated by filtration, washed with of methanol (8 L 2×) and dried under vacuum at 30° C. to give title compound 7 (12.38 kg) (yield=68%).

Step g: Synthesis of 5-[[4-[2-[5-[[[(1,1-dimethylethyl)dimethylsilyl]oxy]ethyl]-2-pyridinyl]ethoxy]phenyl]methyl]-2,4-thiazolidinedione (8)

To a stirred suspension of (5Z)-5-[[4-[2-[5-[[[(1,1-dimethylethyl)dimethylsilyl]oxy]-ethyl]-2-pyridinyl]ethoxy]phenyl]methylene]-2,4-thiazolidinedione (7) (12.38 kg) in THF (25 L) and sodium hydroxide (1N aq, 26 L) was added a solution of cobalt chloride (8.25 g) and of dimethylglyoxime (289 g) in THF (2.65 L) and water (0.66 L). The flask that contained the cobalt chloride/dimethylglyoxime was rinsed with a mixture of THF and water (1/1 v/v, 1 L) and rinse added to the content of the reactor. Thereafter, the suspension was heated at 30° C. and put under a nitrogen atmosphere by applying the sequence of vacuum and flushing with nitrogen (4×). A stock solution of sodium borohydride was prepared by dissolving sodium borohydride (5.0 kg) in a mixture of water (23.3 L) and a solution of sodium hydroxide (1 N aq, 6.2 L), which was put under a nitrogen atmosphere by applying a sequence of vacuum and flushing with nitrogen (3×). This was added to the suspension of compound 7 at a rate of 6.0 L/h. Simultaneously, nitrogen gas-saturated acetic acid was added to the suspension at such rate that a pH of 9.5-10.5 was maintained. After one hour the rate of addition of the sodium borohydride solution was reduced to 2.6 L/h. After addition of 23 L of sodium borohydride solution the addition of sodium borohydride and acetic acid were stopped. The mixture was allowed to cool down to 20° C. and stirred at this temperature overnight. Then acetone (3.1 L) was added slowly. After stirring the reaction mixture for 15 minutes, acetic acid was added until the pH was 5.5-6.0 (5.2 L required). Next, a mixture of ethyl acetate/toluene (1/3 v/v, 37.1 L) was added, well mixed and layers were allowed to settle. The aqueous layer was separated and washed with ethyl acetate/toluene (1/3 v/v, 12.4 L). Both organic extracts were pooled and water (12.4 L) was added, well mixed and layers were allowed to settle. The pH of the aqueous layer was adjusted to 5.5-6 using a 1 M sodium hydroxide solution (aq) and again mixed with the organic layer. Layers were allowed to settle and the organic layer was separated and concentrated under vacuum to give 23.15 kg of yellow oil (crude mixture containing title compound 8 and its borane complex and toluene). The equipment was rinsed with toluene (4 L) to give a solution (4.7 kg) containing crude product in toluene.

The 23.15 kg of the crude mixture containing title compound 8 and its borane complex and toluene and the rinse of 4.7 kg containing product in toluene were pooled, additional toluene (30 L) was added and stirred for 30 minutes. Next, the suspension was filtered and solids were washed with toluene (10 L). The filtrate was submitted to column chromatography (silica gel (70 kg), gradient of toluene to toluene/ethyl acetate 1/1) to give 18.7 kg of a toluene solution containing 10.96 kg of a mixture of 5-[[4-[2-[5-[[[(1,1-dimethylethyl)dimethylsilyl]oxy]ethyl]-2-pyridinyl]ethoxy]phenyl]-methyl]-2,4-thiazolidinedione (8) and its borane complex as a slightly yellow oil (yield=85% from compound 7).

Step h: Synthesis of 5-[[4-[2-[5-(1-hydroxyethyl)-2-pyridinyl]ethoxy]phenyl]-methyl]-2,4-thiazolidinedione hydrochloride (9)

A toluene solution of 18.7 kg containing 10.96 kg of a mixture of 5-[[4-[2-[5-[[[(1,1-dimethylethyl)dimethylsilyl]oxy]ethyl]-2-pyridinyl]ethoxy]phenyl]methyl]-2,4-thiazolidinedione (8) and its borane complex was transferred to a reactor, containers rinsed with toluene (4 L) and rinse also added to the reactor. The level of toluene was reduced to 25% w/w by distillation. Then it was diluted with methanol (54 L) at 20° C. and hydrochloric acid (30%, 6.15 L) was added in about 15 minutes. This solution was heated to 40° C. Two hours after addition, 40 L of volatiles were removed under reduced pressure. Then, acetonitrile (76 L) was added and the mixture was heated at reflux for 0.5 h. Next, the suspension was allowed to cool down to room temperature and stirred for two hours at room temperature. Solids were isolated by filtration, washed with a mixture of acetonitrile/water (20/1 v/v, 8.4 L), acetonitrile (14.5 L) and water (10 L). The isolated solids were transferred to a reactor, water (33 L) added, suspension well stirred and pH adjusted to 2 using 2M hydrochloric acid. The suspension was stirred at 50° C. for two hours and then allowed to cool to room temperature. After one hour at room temperature the solids were isolated by filtration, washed with water (20 L) and dried under vacuum at 40° C. to give 7.77 kg of white solids (crude 9) (yield=85%, not corrected for residual solvents).

Purification of 5-[[4-[2-[5-(1-hydroxyethyl)-2-pyridinyl]ethoxy]phenyl]methyl]-2,4-thiazolidinedione hydrochloride (9)

The crude 5-[[4-[2-[5-(1-hydroxyethyl)-2-pyridinyl]ethoxy]phenyl]-methyl]-2,4-thiazolidine-dione hydrochloride (7.77 kg, crude 9) was dissolved in a mixture of water (35 L) and methanol (124 L) by heating. To this solution at 45° C. was added a suspension of activated charcoal (0.78 kg) in methanol (4 L). Equipment was rinsed with methanol (38.4 L) and water (12.6 L) and rinses added to the reactor. After 0.5 h of stirring at 45° C., the warm suspension was filtered to remove the activated charcoal and filter was washed twice with methanol/water (7/2 v/v, 18 L). The filtrate was concentrated under vacuum at a jacket temperature of 50° C. to a volume of 23.3 L. To the suspension was added butanone (38.9 L). Then volatiles were removed by distillation under simultaneously addition of butanone at such rate that the volume was constant until a process temperature of 76-77° C. was achieved (required 251 L of butanone). Next, heating was stopped and the suspension was allowed to reach room temperature. After 0.75 h at room temperature the solids were isolated by filtration, washed with a mixture of butanone/water (95/5 v/v, 38 L) and butanone (38 L), and dried under vacuum at 40° C. to give 7.14 kg of compound 9 as white solid (yield=92%).

Example 8

Deuteration of 5-[[4-[2-[5-(1-hydroxyethyl)-2-pyridinyl]ethoxy]phenyl]methyl]-2,4-thiazolidinedione

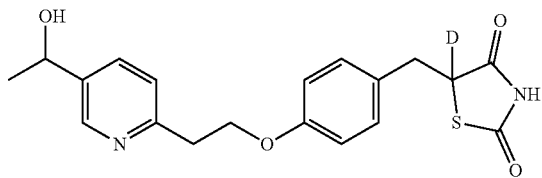 [SMILES: [2H]C1(Cc2ccc(OCCc3ccc(C(C)O)cn3)cc2)SC(=O)NC1=O]

Deuteration of 5-[[4-[2-[5-(1-hydroxyethyl)-2-pyridinyl]ethoxy]phenyl]-methyl]-2,4-thiazolidinedione was conducted as follows:

N,N-(Diisopropyl)aminomethylpolystyrene (1% inorganic agent) (PS-DIEA; 3.2 eq) was added to a solution of 5-[[4-[2-[5-(1-hydroxyethyl)-2-pyridinyl]ethoxy]phenyl]-methyl]-2,4-thiazolidinedione (1.0 eq.) in $CD_3OD$ (60 ml) and the mixture was stirred at room temperature for 7-8 days. The reaction mixture was filtered and washed with $CD_3OD$ (10 ml). The filtrate was concentrated, the residue was diluted with $CH_2Cl_2$ and concentrated completely to afford deuterated 5-[[4-[2-[5-(1-hydroxyethyl)-2-pyridinyl]ethoxy]phenyl]-methyl]-2,4-thiazolidinedione as a white solid (as a mixture of the 4 deuterated isomers). Yield: 73% (440 mg).

ES-MS [M+H]+: 374.1.
$^1$H NMR (400 MHz, DMSO-$d_6$): δ 11.98 (brs, 1H), 8.46 (d, J=1.6 Hz, 1H), 7.67 (dd, J=8.0, 2.4 Hz, 1H), 7.30 (d, J=8.0 Hz, 1H), 7.13 (d, J=8.8 Hz, 2H), 6.86 (d, J=8.4 Hz, 2H), 5.24 (d, J=4.4 Hz, 1H), 4.75 (m, 1H), 4.30 (t, J=6.4 Hz, 2H), 3.31 (m, 1H), 3.14 (t, J=6.4 Hz, 2H), 3.03 (d, J=14.4 Hz, 1H), 1.34 (d, J=6.4 Hz, 3H). Traces of undeuterated starting material was observed.

Example 9

2-(5-(1-((tert-butyldimethylsilyl)oxy)ethyl)pyridin-2-yl)ethan-1-ol (4)

A 20 L flask equipped with mechanical stirrer, under nitrogen atmosphere, was charged with 3160 g (10.0 mol, 1.0 eq.) compound 3 and 8 L of diethylether. The mixture was cooled to −60° C. and 4 L of 2.5M n-BuLi in hexanes (10.0 mol, 1.0 eq. n-BuLi) was added dropwise within 1 hour, while the temperature was kept <−55° C. The mixture was stirred for 1 hour at −80° C. Copper(I)iodide (953 g, 5.0 mol, 0.5 eq.) was added at once, while the temperature was allowed to rise to −43° C. The mixture was cooled back to −55° C. to −60° C. A solution of ethylene oxide (528 g, 12.0 mol, 1.2 eq.) in 900 g diethyl ether at −20° C. (prepared separately in a 2 L vessel) was added dropwise (quickly) within 20 minutes to the reaction-mixture. An exothermic reaction was observed and external cooling with liquid nitrogen was needed to keep the temperature below −20° C. and finally to cool back to −60° C. The mixture was stirred overnight, while the reaction mixture was allowed to reach room temperature.

In a 40 L separation-vessel, 1.2 kg ammonium chloride was dissolved in 6 L of water. The reaction-mixture was poured into the stirred ammonium chloride-solution and stirred for 1 hour to destroy most of the copper-complexes. The layers were separated and the water-layer was extracted with heptane (2×2 L). The combined organic layers were dried over sodium sulfate and filtered over a Celite®-path (to remove more copper-salts). After evaporation of the solvents 3088 g (max. 10.0 mol) crude compound 4 was isolated as a dark brown oil, which was purified by column chromatography, using 22.5 Kg silica. A gradient was applied to elute the product, starting with 80 L heptane/EtOAc 1/I, followed by 20 L EtOAc, 40 L EtOAc/MeOH 95/5, 20 L EtOAc/MeOH 9/1, 20 L EtOAc/MeOH 8/2 and finally 40 L EtOAc/MeOH 7/3. The product fractions with high purity were combined and evaporated to give 1390 g (4.94 mol, yield 9.4%) compound 4 as an brown oil with a HPLC-purity of 99.3%. The disclosure also provides the following particular embodiments designated as [1] for the first embodiment, [2] for the second embodiment, and so on:

[1] A process, comprising
reacting a compound of Formula II:

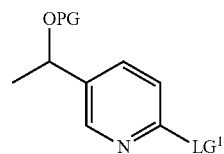

wherein PG is a protecting group selected from silyl protecting groups, tetrahydropyranyl, or methoxymethyl and $LG^1$ is a leaving group,
with ethylene oxide in the presence of
(a) an alkyl lithium and copper(I)iodide or
(b) a Lewis acid selected from the group consisting of $BF_3 \cdot O(Et)_2$, $BBr_3$ and $BCl_3$, and a solvent, wherein
the reaction temperature is maintained below −20° C.,
to give a compound of Formula III:

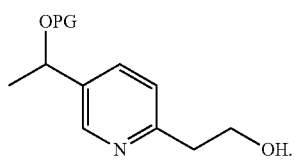

[2] The process of [1], wherein PG is selected from silyl protecting groups.

[3] The process of [1] or [2], wherein PG is an alkyl or aryl silyl group, or a combination thereof.

[4] The process of any one of [1] to [3], wherein PG is a trialkylsilyl group.

[5] The process of any one of [1] to [3], wherein PG is TBDMS, TMS, TES, TIPS, or TBDPS.

[6] The process of any one of [1] to [5], wherein PG is tert-butyldimethylsilyl (TBDMS).

[7] The process of any one of [1] to [6], wherein LG$^1$ is chloride, bromide, iodide, or fluoride.

[8] The process of any one of [1] to [7], wherein LG$^1$ is bromide.

[9] The process of any one of [1] to [8], wherein the reaction is conducted in the presence of an alkyl lithium and copper(I)iodide.

[10] The process of any one of [1] to [9], wherein the alkyl lithium and copper(I)iodide are added while maintaining the reaction temperature at about <−55° C.

[11] The process of any one of [1] to [10], wherein the alkyl lithium is n-butyllithium.

[12] The process of any one of [1] to [8], wherein the reaction is conducted in the presence of a Lewis acid selected from the group consisting of BF$_3$.O(Et)$_2$, BBr$_3$ and BCl$_3$.

[13] The process of any one of [1] to [12], wherein the solvent is a non-polar organic solvent.

[14] The process of any one of [1] to [13], wherein the solvent is diethylether or tert-butyl ether.

[15] The process of any one of [1] to [12], wherein the solvent is a polar organic solvent.

[16] The process of any one of [1] to [12] and [15], wherein the solvent is tetrahydrofuran.

[17] The process of any one of [1] to [16], further comprising isolating said compound of Formula III and optionally purifying the isolated compound of Formula III.

[18] The process of any one of [1] to [17], further comprising reacting said compound of Formula III with R$^1$—Cl, wherein R$^1$ is an organosulfonate, in the presence of a first base to give a compound of Formula IV:

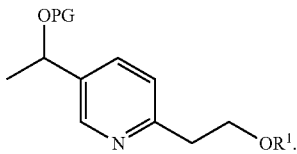

[19] The process of [18], wherein the organosulfonate is a tosyl group (Ts) or a mesyl group (Ms).

[20] The process of [18] or [19], wherein the organosulfonate is a tosyl group.

[21] The process of any one of [18] to [20], wherein the first base is one or more of an amine, a quaternary ammonium salt, tetrabutylammoniumhydroxide, or an alkalimetal hydroxide.

[22] The process of any one of [18] to [21], wherein the first base is a quaternary ammonium salt, optionally in combination with a water solution of an alkalimetal hydroxide.

[23] The process of [22], wherein the first base is tetra-n-butylammonium bromide in aqueous NaOH.

[24] The process of any one of [18] to [23], wherein the reaction is conducted in the presence of a solvent.

[25] The process of any one of claims [18] to [24], further comprising reacting said compound of Formula IV with 4-hydroxybenzaldehyde:

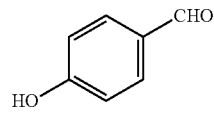

in the presence of a second base and a solvent to give a compound of Formula V:

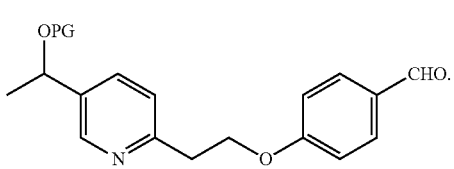

[26] The process of claim 25, wherein the second base is an alkali metal carbonate, a trialkylamine, or an alkali metal alkoxide.

[27] The process of [25] or [26], wherein the second case is K$_2$CO$_3$.

[28] The process of any one of [25] to [27], wherein the solvent is selected from the group consisting of toluene, ethanol, 2-propanol, THF, 2-MeTHF, and water, or a mixture thereof.

[29] The process of any one of [25] to [28], wherein the solvent is a mixture of toluene and ethanol.

[30] The process of any one of [25] to [29], further comprising reacting said compound of Formula V with 2,4-thiazolidinedione:

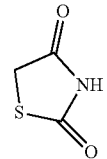

in the presence of piperidine and optionally a solvent, and optionally an organic acid, to give a compound of Formula VI:

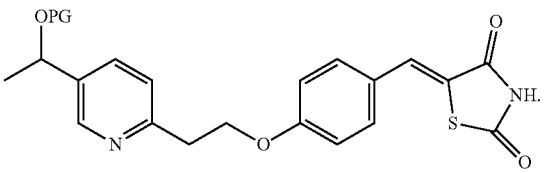

[31] The process of [30], wherein the reaction is conducted in the presence of the solvent.

[32] The process of [30] or [31], wherein the solvent is toluene, a lower alcohol, hexane, or cyclohexane, or a mixture thereof.

[33] The process of any one of [30] to [32], wherein the solvent is toluene or methanol, or a mixture thereof.

[34] The process of any one of [30] to [33], wherein the reaction is conducted in the presence of the organic acid.

[35] The process of any one of [30] to [34], wherein the organic acid is acetic acid or formic acid.

[36] The process of any one of [30] to [35], wherein the reaction is conducted at a temperature of about 45° C. to about 80° C.

[37] The process of any one of [30] to [36], wherein the solvent is methanol and the process is conducted at about 47° C.

[38] The process of any one of [30] to [37], further comprising reducing said compound of Formula VI to give a compound of Formula VII:

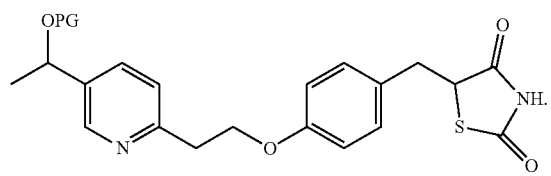

VII

[39] The process of [38], wherein the reduction is conducted by allowing said compound of Formula VI to react with a reducing agent in the presence of a metal ion and a complexing agent for the metal ion.

[40] The process of [38] or [39], wherein the reducing agent is $NaBH_4$.

[41] The process of any one of [38] to [40], wherein the metal ion is $Co^{2+}$.

[42] The process of any one of [38] to [41], wherein the ligand is dimethylglyoxime.

[43] The process of any one of [38] to [42], further comprising deprotecting said compound of Formula VII, and optionally further treating with an acid, to give a compound of Formula I:

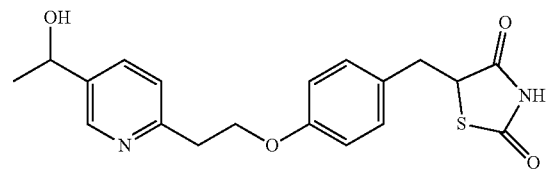

I or a pharmaceutically acceptable salt thereof.

[44] The process of [43], wherein the deprotection of said compound od Formula VII and the salt formation are conducted in two separate steps.

[45] The process of [43], wherein the deprotection of said compound od Formula VII and the salt formation are conducted simultaneously.

[46] The process of any one of [43] to [45], wherein said compound of Formula I is isolated as its pharmaceutically acceptable salt.

[47] The process of any one of [43] to [46], wherein said compound of Formula I is 5-[[4-[2-[5-(1-hydroxyethyl)-2-pyridinyl]ethoxy]phenyl]methyl]-2,4-thiazolidinedione hydrochloride salt.

[48] The process of [1], wherein said compound of Formula II is prepared by protecting the hydroxyl group of a compound of Formula VIII:

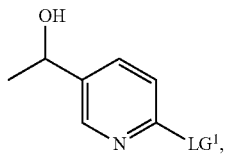

VIII wherein $LG^1$ is a leaving group, with a protecting group PG, wherein PG is selected from silyl protecting groups, tetrahydropyranyl, or methoxymethyl, to give the compound of Formula II.

[49] The process of [48], wherein said compound of Formula VIII reacted with a silyl chloride selected from the group consisting of TBDMS-Cl, TMS-Cl, TBDPS-Cl, and TIPS-Cl and imidazole at high concentration in DMF.

[50] The process of [48] or [49], wherein said compound of Formula VIII is prepared by reacting a compound of Formula IX:

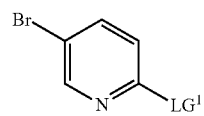

IX wherein $LG^1$ is a leaving group, with $CH_3CHO$ in the presence of an alkylmagnesiumhalide and a solvent to give the compound of Formula VIII.

[51] A compound of Formula III:

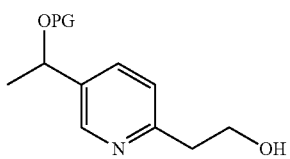

III wherein PG is a protecting group selected from silyl protecting groups, tetrahydropyranyl, or methoxymethyl, prepared by the process as in any one of [1] to [17].

[52] A compound of Formula I:

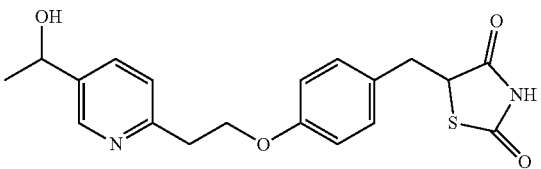

I or a pharmaceutically acceptable salt thereof, prepared by the process as in any one of [1] to [50].

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A process, comprising
   (i) combining an alkyl lithium and a compound having Formula II:

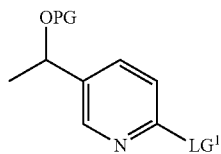

in a solvent at a temperature from about −20° C. to about −85° C. to give a first reaction mixture, wherein PG is a protecting group and $LG^1$ is bromide or iodide;
   (ii) adding ethylene oxide as is to said first reaction mixture at said temperature to give a second reaction mixture; and
   (iii) adding a copper(I)salt to said second reaction mixture at said temperature to give a third reaction mixture comprising a compound having Formula III:

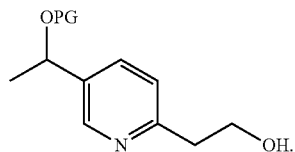

2. The process of claim 1, wherein PG is a protecting group selected from the group consisting of a silyl protecting group, tetrahydropyranyl, methoxymethyl, and benzyl.

3. The process of claim 2, wherein PG is selected from silyl protecting groups.

4. The process of claim 3, wherein PG is an alkyl or aryl silyl group, or a combination thereof.

5. The process of claim 4, wherein PG is a trialkylsilyl group.

6. The process of claim 5, wherein PG is TBDMS, TMS, TES, TIPS, or TBDPS.

7. The process of claim 6, wherein PG is tert-butyldimethylsilyl (TBDMS).

8. The process of claim 1, wherein $LG^1$ is iodide.

9. The process of claim 1, wherein $LG^1$ is bromide.

10. The process of claim 1, wherein the alkyl lithium is $C_{1-6}$ alkyl lithium.

11. The process of claim 10, wherein the alkyl lithium is n-butyllithium.

12. The process of claim 1, wherein the solvent is selected from the group consisting of a non-polar aprotic organic solvent and a polar aprotic organic solvent, or a mixture thereof.

13. The process of claim 12, wherein the solvent is a non-polar aprotic organic solvent.

14. The process of claim 13, wherein the solvent is methyl tert-butyl ether.

15. The process of claim 1, wherein said third reaction mixture is allowed to warm to a temperature of 20° C.-25° C.

16. The process of claim 15, wherein said third reaction mixture is kept at 20° C.-25° C. for at least 8 hours.

17. The process of claim 1, further comprising isolating said compound of Formula III and optionally purifying the isolated compound of Formula III.

18. The process of claim 17, wherein the isolated compound of Formula III is purified by recrystallization.

* * * * *